United States Patent
Katra et al.

(10) Patent No.: US 10,542,939 B2
(45) Date of Patent: Jan. 28, 2020

(54) SYSTEM AND METHODS OF PROCESSING ACCELEROMETER SIGNALS

(71) Applicant: Medtronic Monitoring, Inc., San Jose, CA (US)

(72) Inventors: Rodolphe Katra, Blaine, MN (US); Matthew Edelman, Lino Lakes, MN (US); Scott Williams, Minneapolis, MN (US); Niranjan Chakravarthy, Eden Prairie, MN (US); Arthur Lai, Minnetonka, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 582 days.

(21) Appl. No.: 15/350,849

(22) Filed: Nov. 14, 2016

(65) Prior Publication Data

US 2018/0132793 A1    May 17, 2018

(51) Int. Cl.
    *A61B 5/02*    (2006.01)
    *A61B 5/00*    (2006.01)
    (Continued)

(52) U.S. Cl.
    CPC .......... *A61B 5/7246* (2013.01); *A61B 5/0002* (2013.01); *A61B 5/046* (2013.01);
    (Continued)

(58) Field of Classification Search
    CPC ... A61B 5/7285; A61B 5/6847; A61B 5/1118; A61B 5/1116; A61B 5/0464;
    (Continued)

(56) References Cited

U.S. PATENT DOCUMENTS 6,327,499 B1 * 12/2001 Alt ................. A61N 1/36542
                                                  607/4
6,529,771 B1    3/2003 Kieval et al.
(Continued)

FOREIGN PATENT DOCUMENTS

| WO | 0157877 A1 | 8/2001 |
| WO | 2005048824 A2 | 6/2005 |
| WO | 2014135187 A1 | 9/2014 |

OTHER PUBLICATIONS

Gerald Bieber, Thomas Kirste, and Michael Gaede. 2014. Low sampling rate for physical activity recognition. In Proceedings of the 7th International Conference on PErvasive Technologies Related to Assistive Environments (PETRA '14). ACM, New York, NY, USA, Article 15, 8 pages. (Year: 2014).*
(Continued)

*Primary Examiner* — Eric J Messersmith
(74) *Attorney, Agent, or Firm* — Shumaker & Sieffert, P.A.

(57) ABSTRACT

Embodiments of the present disclosure describe a method of monitoring a patient comprising generating an accelerometer signal of a patient via a patient medical device and capturing and sampling the accelerometer signal at a sampling rate that utilizes non-regular timing intervals. Embodiments further describe a patient medical device comprising sensors for monitoring an accelerometer signal of a patient and circuitry for sampling the accelerometer signal at a sampling rate that utilizes non-regular timing intervals. Embodiments also describe a method of processing physiological signals comprising monitoring ECG signals and accelerometer signals of a patient via a patient medical device and capturing an ECG segment and sampling the accelerometer signal at a sampling rate that utilizes non-regular timing intervals.

22 Claims, 19 Drawing Sheets

(51) Int. Cl.
*G16H 20/30* (2018.01)
*G16H 40/63* (2018.01)
*A61B 5/046* (2006.01)
*A61B 5/0464* (2006.01)
*A61B 5/11* (2006.01)
*A61B 5/22* (2006.01)
*A61B 5/16* (2006.01)

(52) U.S. Cl.
CPC .......... *A61B 5/0464* (2013.01); *A61B 5/1116* (2013.01); *A61B 5/1118* (2013.01); *A61B 5/6832* (2013.01); *A61B 5/6847* (2013.01); *A61B 5/7275* (2013.01); *A61B 5/7282* (2013.01); *A61B 5/7285* (2013.01); *G16H 20/30* (2018.01); *G16H 40/63* (2018.01); *A61B 5/0022* (2013.01); *A61B 5/168* (2013.01); *A61B 5/22* (2013.01); *A61B 5/4076* (2013.01); *A61B 2505/07* (2013.01); *A61B 2560/0209* (2013.01); *A61B 2562/0219* (2013.01)

(58) Field of Classification Search
CPC ..... A61B 5/046; A61B 5/6832; A61B 5/7282; A61B 5/7275; A61B 5/0002; A61B 5/7246; G16H 20/30; G16H 40/63
See application file for complete search history.

(56) References Cited

U.S. PATENT DOCUMENTS

| | | |
|---|---|---|
| 7,313,440 B2 | 12/2007 | Miesel |
| 7,697,983 B1 | 4/2010 | Oza |
| 8,016,776 B2 | 9/2011 | Bourget et al. |
| 8,135,473 B2 | 3/2012 | Miesel et al. |
| 8,145,307 B2 | 3/2012 | Zhang et al. |
| 8,444,578 B2 | 5/2013 | Bourget et al. |
| 8,460,189 B2 | 6/2013 | Libbus et al. |
| 8,475,370 B2 | 7/2013 | McCombie et al. |
| 8,688,221 B2 | 4/2014 | Miesel et al. |
| 8,755,874 B2 | 6/2014 | Bjorling et al. |
| 2006/0264767 A1 | 11/2006 | Shennib |
| 2007/0129622 A1 | 6/2007 | Bourget et al. |
| 2008/0071150 A1* | 3/2008 | Miesel ............... A61B 5/1116 600/301 |
| 2009/0076397 A1 | 3/2009 | Libbus et al. |
| 2009/0292227 A1* | 11/2009 | Scholten ............. A61B 5/0031 600/595 |
| 2016/0022141 A1* | 1/2016 | Mittal ................. A61B 5/0002 340/870.07 |
| 2016/0278659 A1 | 9/2016 | Kaib et al. |
| 2017/0056669 A1* | 3/2017 | Kane ................ A61N 1/36585 |

OTHER PUBLICATIONS

Notification of Transmittal of the International Search Report and the Written Opinion of the International Searching Authority, or the Declaration for PCT/US2017/061481 dated Jan. 23, 2018.

Baek, et al., "Posture Monitoring System for Context Awareness in Mobile Computing", IEEE Transactions on Instrumentation and Measurement, vol. 59, No. 6, Jun. 6, 2010, 1589-1599.

Najafi, et al., "Ambulatory System for Human Motion Analysis Using a Kinematic Sensor: Monitoring of Daily Physical Activity in the Elderly", IEE Transaction on Biomedical Engineering, vol. 50, No. 6, Jun. 6, 2003, 711-723.

Preece, et al., "Activity identification using body-mounted sensors-a review of classification techniques", Physiological Measurement, Institute of Physics Publishing, Bristol, GB, vol. 30, No. 4, Apr. 2, 2009, R1-R33.

"Vital Connect Partner with Life Watch to Enhance Remote Cardiac Monitoring Services", Healthcare IT News, http://www.healthcareitnews.com/press-release/vital-connect-partners-lifewatch-enhance-remote-cardiac-monitoring-services, Nov. 14, 2014.

Response to European Communication pursuant to Rules 161(1) and 162, filed Nov. 22, 2019, for European Patent Application No. 17817334.0, 3 pages.

* cited by examiner

SYSTEM AND METHODS OF PROCESSING ACCELEROMETER SIGNALS

TECHNICAL FIELD

The present disclosure is generally related to patient medical devices and in particular to those utilizing an accelerometer.

BACKGROUND

In diagnosing arrhythmias, diagnostically relevant information includes a type of arrhythmia and a rate during the arrhythmia, as well as a patient's symptoms, activity level, and posture before and after the arrhythmia. While cardiac monitors may be utilized to detect various types of arrhythmias and a patient's rate during the arrhythmia, current monitors fail to provide accelerometer-derived objective patient activity levels and posture before and after an arrhythmia. Generally, this is because cardiac monitoring—particularly ambulatory monitoring—includes long-term monitoring of ECG signals and the amount of data generated by an accelerometer in an ambulatory setting is cost prohibitive with respect to transmission costs and battery longevity, among other things. Instead, physicians and other medical professionals either rely on the patient to record symptoms and activity levels in a patient diary, or the patient's recollection of symptoms and activity levels at a later date, for example, during an examination or a phone call from the monitoring center to note symptoms when the patient trigger is pressed. While in some instances a time of day at which an arrhythmia occurred is relied upon to estimate a patient's activity level and/or posture, time of day is a poor surrogate for activity information recorded in real-time.

Current devices that monitor patient activity could also suffer from errors due to the location of the device being on a periphery of the patient, such as an arm or wrist. For example, current devices may monitor patient activity via hand-only movement, but this introduces error, distorts signals, and sacrifices accuracy. Furthermore, current devices that attach to an article of clothing (e.g., a belt clip/holster or lanyard) do not provide reliable measurements of patient activity since they are not adhered to nor implanted in a patient's body. In addition, utilization of independent devices for monitoring patient activity and ECG, respectively, without a shared common clock, could result in problems synchronizing detected activity levels and arrhythmias.

It would therefore be desirable to provide a system and method that may be adhered to or implanted in a patient's body, reduce the amount of accelerometer data needed to continuously track and accurately detect a patient's activity and posture, and synchronize results with one another to enhance a diagnosis of arrhythmia.

SUMMARY

In general, embodiments of the present disclosure describe systems and methods of processing accelerometer signals and enhancing arrhythmia diagnosis with objective activity measures.

Accordingly, embodiments of the present disclosure describe a method of monitoring a patient comprising monitoring an accelerometer signal of a patient via a patient medical device and sampling the accelerometer signal at a sampling rate that utilizes non-regular timing intervals.

Embodiments of the present disclosure further describe a patient medical device comprising sensors for monitoring an accelerometer signal of a patient. The patient medical device further comprises circuitry for sampling the accelerometer signal at a sampling rate that utilizes non-regular timing intervals.

Embodiments of the present disclosure also describe a method of processing physiological signals comprising monitoring ECG signals and accelerometer signals of a patient via a patient medical device, and capturing an ECG segment and sampling the accelerometer signal at a sampling rate that utilizes non-regular timing intervals.

The details of one or more examples are set forth in the description below. Other features, objects, and advantages will be apparent from the description and from the claims.

DETAILED DESCRIPTION

The present invention relates to systems and methods of processing an accelerometer signal. In particular, the present invention relates to processing accelerometer signals at a reduced sampling rate (e.g., downsampling the signal) and/or at non-regular timing intervals (e.g., via a timing jitter) sufficient to reduce an amount of data needed to continuously track and accurately detect a patient's activity and posture. In this way, the present invention balances the costs associated with communicating or processing large volumes of information collected throughout a monitoring duration (e.g., an amount of transmitted data, battery preservation, etc.) with the presentation of granular temporal activity and posture information. In addition, the present invention combines diagnostically relevant information of an activity profile (e.g., a patient's activity level and/or posture before, during, and/or after a clinically relevant episode) with other physiological data, such as electrocardiogram signals/segments, to determine a level of debilitation, prioritize, improve a diagnosis, and/or determine a severity of a clinically relevant episode (e.g., arrhythmia).

Figure 1:
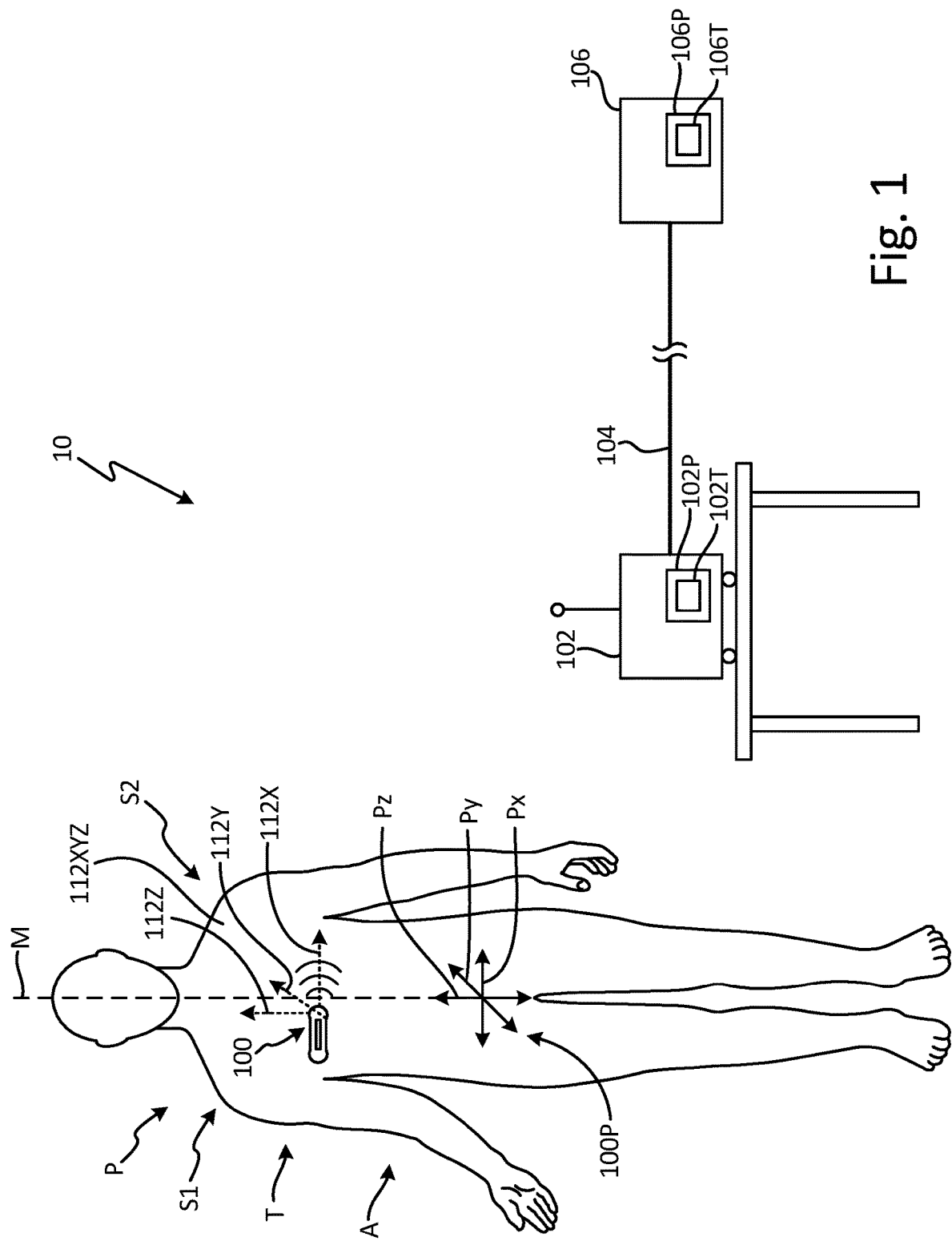
FIG. 1 is a schematic view of a patient and a patient monitoring system, according to one or more embodiments of the present disclosure.

FIG. 1 is a schematic view of a patient P and a monitoring system 10, according to an embodiment of the present disclosure. Patient P includes a midline M, a first side S1 (e.g., a right side), and a second side S2 (e.g., a left side). Monitoring system 10 includes a patient medical device 100, gateway 102, and remote monitoring center 106. In the embodiment shown in FIG. 1, patient medical device 100 is an adherent device that is attached to the skin of the patient. In other embodiments (not shown in FIG. 1), patient medical device 100 may be an implantable device, an insertable device, an injectable device, and/or a wearable device, such as a Holter monitor (collectively referred to as a medical device). Exemplary embodiments of suitable medical devices are described in more detail with respect to FIGS. 1, 8, and 9. In general, medical device 100 is described herein as performing a monitoring function, but in other embodiments may be configured to provide treatment as well.

Medical device 100 can be adhered/injected/inserted/worn by patient P at many locations. In many embodiments, adherent device 100 is adhered to one side of a thorax of patient P (e.g., a first side S1 (shown in FIG. 1) or a second side S2 (not shown)). The location of medical device 100 can vary in other embodiments and depend on the physiological parameters of patient P being monitored. The physiological parameters being monitored by medical device 100 may include accelerometer signals to determine activity levels and body posture of a patient P and electrocardiogram (ECG) signals to detect arrhythmias, such as tachycardia and/or bradycardia and/or atrial fibrillation, as well as bioimpedance, respiration, blood pressure, etc. A benefit of medical device 100 and its various embodiments is that it may be utilized to collect objective and/or quantifiable measurements of an ambulatory patient's activity levels and body posture to prioritize, and improve a diagnosis and/or determine a severity of, an arrhythmic episode. In addition, medical device 100 and its various embodiments may be utilized to determine a level of debilitation of a patient following a clinically relevant episode.

As shown in FIG. 1, medical device 100 may be aligned and/or oriented with respect to one or more axes of patient P via a patient coordinate system 100P. For example, patient P may include a horizontal axis $P_x$ that extends laterally from one side of the patient to the other side of the patient, for example, from side S1 to side S2 across midline M. Patient P may include an anterior posterior axis $P_y$ that extends from the front of the patient (e.g., anterior) to the back of the patient (e.g., posterior). Patient P may include a vertical axis $P_z$ that extends vertically along the patient, for example, vertically along the midline of the patient from the feet of the patient toward the head of the patient. In many embodiments, horizontal axis $P_x$, anterior posterior axis $P_y$, and vertical axis $P_z$ may include a right-handed triple of orthogonal coordinate references.

In embodiments in which medical device 100 is an adherent device, adherent device 100 may include a 3D coordinate reference system 112XYZ for aligning and/or orienting the adherent device 100 with the patient coordinate system 100P. For example, adherent device 100 may include a 3D coordinate reference system 112XYZ. Adherent device 100 may include an x-axis 112X for alignment with horizontal axis $P_x$ of the patient or for alignment at an angle with horizontal axis $P_x$ of the patient (e.g., to capture a wearable sensor's lead II application angle), a y-axis 112Y for alignment with anterior posterior axis $P_y$ of the patient, and z-axis 112Z for alignment with vertical axis $P_z$. Adherent device 100 may also be aligned at an angle with one or more of horizontal axis $P_x$, anterior posterior axis $P_y$, and vertical axis $P_z$ to better correlate the ECG and accelerometer data with physiological signals relevant to the condition or conditions of interest. Coordinate reference system 112XYZ may include a right-handed triple, although other non-orthogonal and orthogonal reference systems may be used.

While adherent device 100 is discussed in more detail below with respect to FIG. 8, in many embodiments, adherent device 100 may include a cardiac monitor for detecting arrhythmias and an accelerometer for determining patient activity and body posture. For example, adherent device 100 may include one or more sensors and one or more circuitry for monitoring (e.g., sensing) ECG signals and accelerometer signals and for capturing (e.g., collecting and storing) and processing (e.g., analyzing) ECG segments and accelerometer data. In many embodiments, ECG signals and accelerometer signals may be monitored via one or more sensors provided on the same medical device. By providing one or more sensors for measuring ECG signals and accelerometer signals on the same medical device, the accelerometer and cardiac monitoring device may share a common clock to more accurately synchronize activity levels with arrhythmias. In addition, many embodiments include a medical device located on a thorax of the patient. By measuring accelerometer signals, in addition to ECG signals, from a thorax of the patient, the medical device of the present disclosure minimizes errors in comparison to devices in which a patient's activity is monitored via sensors located on a periphery, such as on a limb, arm, and/or wrist. In some embodiments, accelerometer signals and ECG signals are measured via common sensors (e.g., the same sensors). In other embodiments, separate sensors may be utilized to monitor, capture, and process each of ECG signals and accelerometer signals. In many embodiments, the activity sensor includes a three-axis accelerometer to measure an activity level and body posture of a patient. For example, accelerometer measurements may include one or more of an inclination, a position, an orientation, or acceleration of the patient in three dimensions. In other embodiments, the activity sensor includes one or more of a piezoelectric accelerometer, a capacitive accelerometer, and an electromechanical accelerometer.

In embodiments with an activity sensor, the activity sensor may include a three-axis accelerometer with at least one measurement axis. In some embodiments, the three-axis accelerometer may include an x-axis, a y-axis, and a z-axis, each of which may be sensitive to gravity such that the orientation of the accelerometer can be determined in relation to gravity. In some embodiments, the three-axis accelerometer may utilize the same sensors (e.g., electrodes) for monitoring ECG signals. In other embodiments, the three-axis accelerometer may be aligned with sensors (e.g., electrodes) for monitoring ECG signals. In some embodiments, the three-axis accelerometer may include an x-axis aligned with one or more of the x-axis 112X of adherent device 100 and the horizontal axis $P_x$ of patient coordinate system 100P, a y-axis aligned with one or more of the y-axis 112Y of adherent device 100 and the anterior posterior axis $P_y$ of patient coordinate system 100P, and a z-axis aligned with one or more of the z-axis 112Z of adherent device 100 and the vertical axis $P_z$ of patient coordinate system 100P. In some embodiments, the axes of the three-axis accelerometer may be aligned in a predetermined, parallel, or non-parallel configuration.

In the embodiment shown in FIG. 1, adherent device 100 communicates wirelessly with remote monitoring center 106. Adherent device 100 may communicate directly (via a cellular or Wi-Fi network, or via Bluetooth connectivity, etc.), or indirectly through an intermediate device or gateway 102. The determination of which operations (e.g., monitoring, capturing, and/or processing) are performed locally (e.g., at adherent device 100) and which operations are performed remotely (e.g., at remote monitoring center 106) may depend on a balancing of tradeoffs. For example, in some embodiments, the determination may require balancing a cost of transmitting data with an interest in preserving battery life. In many embodiments, the determination properly balances these costs by minimizing the amount of accelerometer data transmitted to the remote monitoring center 106. In other embodiments, the determination includes balancing and/or considering other factors, such as labor costs, storage costs, urgency, accuracy, and efficiency.

Physiological data may be processed (e.g., analyzed) locally by medical device 100 (e.g., at adherent device 100A), or remotely by gateway 102 and/or remote monitoring center 106 (or similar platform separate from medical device 100). Processing of physiological data (e.g., ECG signals/segments, accelerometer signals/data/information) may include monitoring physiological signals, capturing physiological data (e.g., in response to a triggering event), processing physiological data at a reduced sampling rate and/or at non-regular timing intervals, communicating (via a cellular or Wi-Fi network, or via Bluetooth connectivity) captured and/or processed physiological data to an external processing center such as gateway 102 and/or remote monitoring center 106, detecting clinically relevant episodes (e.g., arrhythmias), and/or computing/estimating/deriving physiological information (e.g., patient activity and/or body posture) from physiological data. Any of the above processes and/or analyses may be performed locally and/or remotely.

In many embodiments, adherent device 100 locally monitors accelerometer signals, captures all accelerometer signals, processes the accelerometer signals at a reduced sampling rate and/or at non-regular timing intervals, and communicates (via a cellular or Wi-Fi network, or via Bluetooth connectivity) the processed accelerometer signals to an external processing center such as gateway 102 and/or remote monitoring center 106. At the external processing center, the raw communicated data is further processed to extract information including patient activity levels and/or body posture to construct an activity profile with activity intensities. In addition, the extracted information may be combined and presented with other clinically relevant information to prioritize, and improve a diagnosis and/or determine a severity level of, clinically relevant episodes. In other embodiments, any combination of locally and/or remotely performed processes may be achieved.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example, with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by human experts to verify accuracy. Reports may then be generated at remote monitoring center 106 for communication to the patient's physician or care provider. In one embodiment, in addition to one-way communication from medical device 100 to gateway 102 and/or remote monitoring center 106, remote monitoring center 106 may communicate/push baseline data to medical device 100, either to program/initialize medical device 100 or update the baseline data stored by medical device 100.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG and accelerometer signals—monitored by medical device 100 may be analyzed by one or more of the distributed processors included as part of medical device 100, gateway 102, and/or remote monitoring center 106.

Figure 2A:
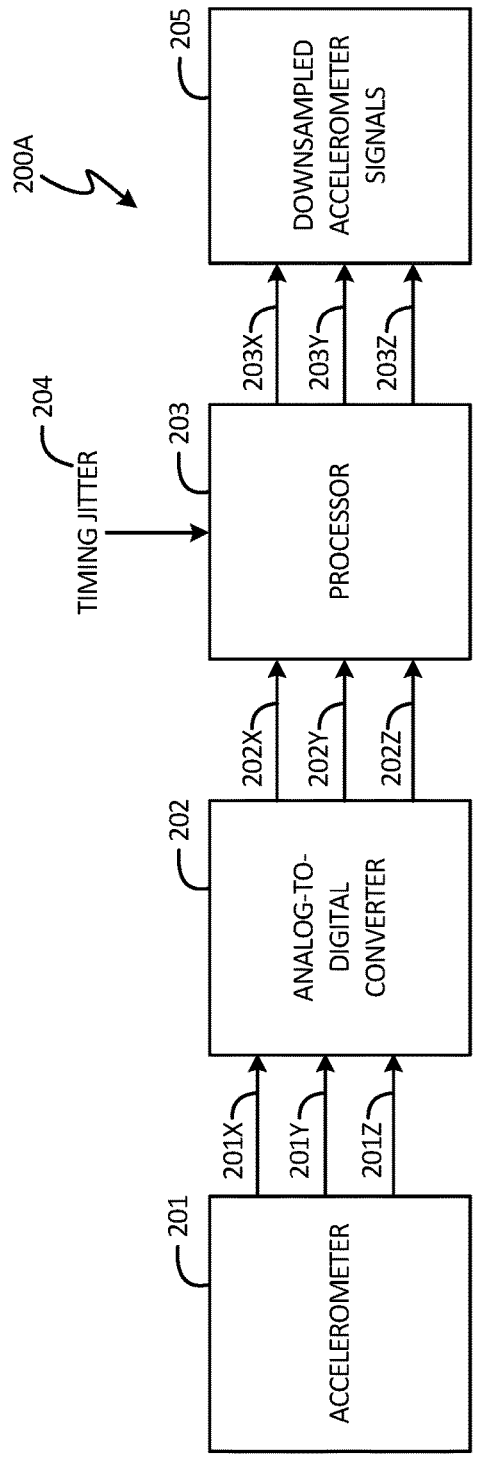
FIGS. 2a-2b include schematic diagrams of systems for sampling an accelerometer signal, according to one or more embodiments of the present disclosure.
Figure 2B:
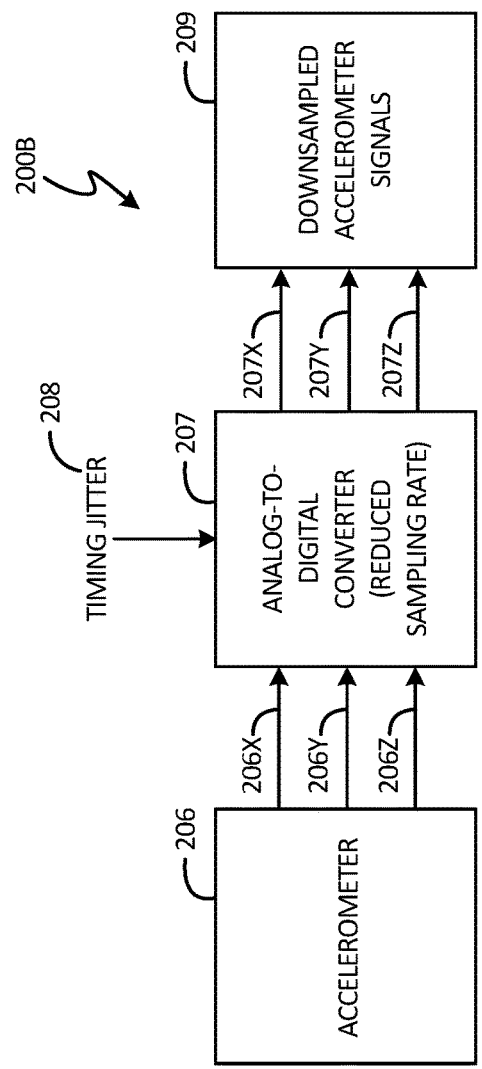

FIGS. 2a-2b include schematic diagrams of systems for sampling an accelerometer signal, according to one or more embodiments of the present disclosure. Any of the medical devices and methods of the present disclosure may utilize the systems illustrated in FIGS. 2a-2b.

FIG. 2a is a schematic diagram of a system 200A for sampling an accelerometer signal at a first sampling rate and at a second reduced sampling rate, according to an embodiment of the present disclosure. The system includes an accelerometer 201, an analog-to-digital converter 202, a processor 203, and a timing jitter 204. The system 200A produces an accelerometer signal 205 that has been downsampled without an anti-aliasing pre-filter and with a timing jitter (e.g., at non-regular timing intervals). The accelerometer 201 may produce an accelerometer signal with at least one axis value. As shown in FIG. 2a, in many embodiments, the accelerometer signal includes three axis values, including an x-axis value 201X, a y-axis value 201Y, and a z-axis value 201Z. The accelerometer signal may be communicated to the analog-to-digital converter 202, where each of the three values of the accelerometer signal may be sampled at a first sampling rate to produce an x-axis value 202X, a y-axis value 202Y, and a z-axis value 202Z. These are communicated to the processor 203 and sampled at a second sampling rate with a timing jitter 204 (e.g., at non-regular timing intervals), wherein the second sampling rate is much less than the first sampling rate. In some embodiments, the same timing jitter may be applied to each of the x-axis value 202X, the y-axis value 202Y, and the z-axis value 202Z. In other embodiments, a different timing jitter may be applied to each of one or more of the x-axis value 202X, the y-axis value 202Y, and the z-axis value 202Z. The signals from the processor may include an x-axis value 203X, a y-axis value 203Y, and a z-axis value 203Z, which collectively refer to the downsampled accelerometer signal 205.

FIG. 2b is a schematic diagram of a system 200B for sampling an accelerometer signal at a reduced sampling rate, according to an embodiment of the present disclosure. FIG. 2b is similar to the embodiment illustrated in FIG. 2a, except that instead of utilizing a processor for sampling the accelerometer signal at a second reduced sampling rate, the accelerometer signal from the accelerometer 206 is immediately sampled at a reduced sampling rate without an anti-aliasing low-pass filter. For example, accelerometer signals may include an x-axis value 206X, a y-axis value 206Y, and a z-axis value 206Z. The accelerometer signals from accelerometer 206 may be communicated to an analog-to-digital converter 207 where each of the three values are sampled at a reduced sampling rate with a timing jitter 208 (e.g., at non-regular timing intervals). The sampled signals include an x-axis value 207X, a y-axis value 207Y, and a z-axis value 207Z, which collectively refer to the down-sampled accelerometer signal 209. In many embodiments, the reduced sampling rate is a sampling rate that is much less than 100 Hz. In other embodiments, any sampling rate may be utilized by analog-to-digital converter 207.

Figure 3A:
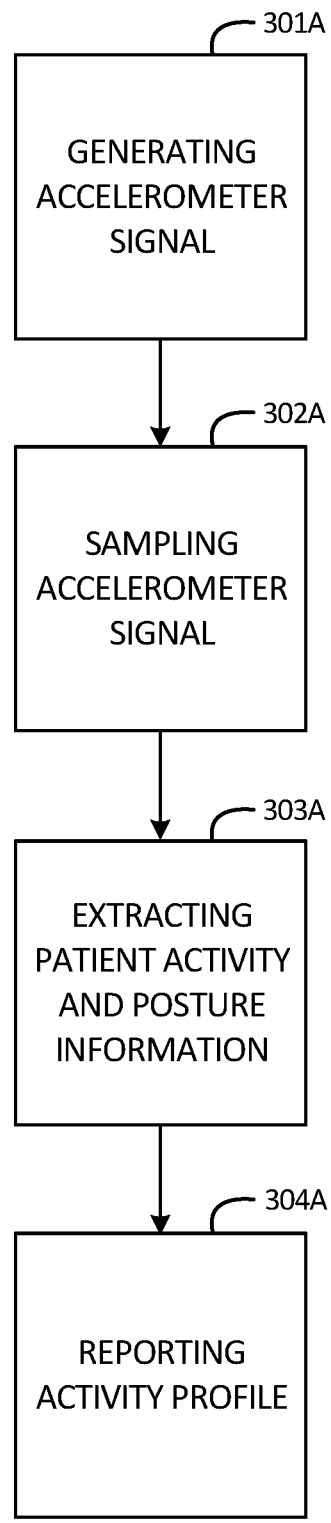
FIGS. 3a-3b are flowcharts of methods of monitoring an ambulatory patient, according to one or more embodiments of the present disclosure.

FIG. 3a is a flowchart of a method of monitoring a patient, according to an embodiment of the present disclosure. Any of the medical devices of the present disclosure may be utilized to implement the method illustrated in FIG. 3a.

At step 301A, an accelerometer signal of a patient is generated via a medical device. In many embodiments, the accelerometer signal is generated from an accelerometer. In other embodiments, the accelerometer signal is monitored via a medical device. In addition to generating and/or monitoring accelerometer signals, the medical device may generate and/or monitor ECG signals, hydration impedance signals, respiration impedance signals, blood pressure, and/or any other physiological signals discussed herein and/or within the knowledge of one of skill in the art.

At step 302A, accelerometer signals are sampled at a sampling rate that utilizes non-regular timing intervals (e.g., a timing jitter). In many embodiments, the accelerometer signal (e.g., accelerometer values along each of three axes in a three-axis accelerometer) is sampled at a reduced sampling rate and/or at non-regular timing intervals sufficient to retain activity and/or posture information of a patient and to reduce an amount of data needed to continuously track and accurately detect a patient's activity and posture. In many embodiments, this data may be stored and communicated to a remote monitoring center where patient activity and posture information is extracted and used to construct an activity profile. In this way, the medical device of the present disclosure may reduce costs associated with communicating data generated at high sampling rates (e.g., 100 Hz). In addition, the medical device of the present disclosure may improve and/or preserve battery longevity, among other things. The medical device of the present disclosure finds an optimal balance between the amount of transmitted data and the presentation of granular temporal activity and posture information.

Traditionally, downsampling a signal requires use of a low-pass filter to avoid aliasing effects. However, low-pass filters result in the loss of information provided in the high-frequency range. With respect to accelerometers, patient activity information is generally provided in the higher frequencies and patient posture information is generally provided in the lower frequencies of the accelerometer signal. Use of a low-pass filter therefore results in a loss of high frequency content indicative of patient activity. To prevent the loss of high frequency content, an embodiment of the present invention foregoes application of a low-pass filter. A timing jitter is introduced into the sampling frequency that results in the interval between samples being non-regular. As a result, higher frequencies fold into the lower frequencies while retaining activity information provided in the high-frequency range. Although the introduction of timing jitter to the downsampling process may not allow for reconstruction of the high frequency signal, it will allow for determination of the power associated with the higher frequency components of the accelerometer signal, which is sufficient for determining activity level of the patient.

As a result, the accelerometer signal may be sampled at a reduced rate and/or at non-regular timing intervals to reduce an amount of data to be transmitted while also ensuring a patient's activity and posture may be continuously tracked and accurately detected. In some embodiments, the accelerometer signal/data may be sampled at a reduced sampling rate of about 0.25 Hz (or about 1 sample every 4 seconds). In some embodiments, the accelerometer signal/data may be sampled at non-regular timing intervals via a timing jitter. For instance, sampling with a timing jitter may include sampling at $t(t_1+\Delta)$, $t(t_2+\Delta)$, $t(t_3+\Delta)$, . . . , $t(t_n+\Delta)$, where $\Delta$ is a random integer from a uniform random number generator or chosen from a pseudo-random pre-chosen sequence (e.g., [−1, 1, 2, 5, 2, −2, 2, −4]). According to this embodiment, the accelerometer signal may be processed by capturing 1 sample every 4 seconds plus or minus $\Delta$. In other embodiments, any reduced sampling rate and/or downsampling rate may be utilized.

In one embodiment, the accelerometer signal may be sampled at a reduced sampling rate and/or at non-regular timing intervals via an analog-to-digital converter, and all of the data from the signals sampled at the reduced rate and/or at non-regular timing intervals may be stored in memory. For example, the accelerometer signal may be sampled at a sampling rate of about 0.25 Hz and/or at non-regular timing intervals (i.e., introduced timing jitter) to reduce an amount of data from the accelerometer signal stored in memory. A benefit of storing all sampled accelerometer signals in memory is that this data may be available for analysis, as the clinical relevance of the information may not be determinable until a period of time in the future, such as at a time of a future arrhythmia.

In another embodiment, the accelerometer signal may be sampled at a first sampling rate and at a second sampling rate. The first sampling rate may be much higher than the second sampling rate. For example, the accelerometer signal may be sampled at 100 Hz (e.g., a first sampling rate) and that signal may be downsampled at 0.25 Hz (e.g., a second sampling rate) to reduce an amount of data from the accelerometer. In this embodiment, all of the data from the downsampled accelerometer signal may be stored in memory.

In other embodiments, accelerometer signals/data generated over a predetermined period of time are continuously sampled and stored (e.g., temporarily stored) in memory (e.g., looping memory), and prospective accelerometer signals may be sampled in response to a triggering event. For example, in some embodiments, accelerometer signals generated from a period of about the last 30 minutes may be continuously sampled and stored in memory, with the oldest signals that have been stored being discarded and/or replaced over time. In some embodiments, prospective accelerometer signals may be sampled and stored in memory in response to a triggering event. In some embodiments, depending on the detected physiological episode (e.g., arrhythmia), the accelerometer signals stored in looping memory and/or prospective accelerometer signals may be sampled, captured, and processed in response to a triggering event.

Generally, a triggering event may include a patient-triggered event or an automatically triggered event. A patient-triggered event may include an event in which a patient experiences an onset of symptoms and manually triggers capture of physiological data. In some embodiments, upon experiencing an onset of symptoms, a patient may manually trigger capture of accelerometer signals and/or ECG segments. In other embodiments, upon experiencing an onset of symptoms, a patient may manually trigger capture of any type of physiological data.

An automatically triggered event may include an event in which physiological data is captured without human intervention upon monitoring and/or detecting physiological data defining an automatically triggered event. In some embodiments, an automatically triggered event may be defined as abnormal physiological signals. For example, an abnormal physiological signal may include one or more of an abnormal heart rhythm, an abnormal heart beat, an abnormal ECG signal/segment, an abnormal morphology, and a significant ECG change. To detect abnormal physiological signals, monitored physiological signals may be compared to threshold levels, population-based baseline data, and/or patient-specific baseline data. For example, threshold levels may include an upper heart rate limit and/or a lower heart rate limit, and population-based and/or patient-specific data relating to heart rhythm, heart rate, ECG morphology, etc. In other embodiments, recently monitored and/or previously captured physiological data may be used to define automatically triggering events.

The accelerometer data that is captured may include prospective accelerometer signals, recent accelerometer data stored in memory, and combinations thereof. In some embodiments, the accelerometer data from prospective accelerometer signals may include data from accelerometer signals following a triggering event. In some embodiments, the accelerometer data that is captured may include recent accelerometer data stored in memory (e.g., "looping" memory) preceding a triggering event. For example, looping memory may include about t minutes (e.g., about 15 minutes) of previously monitored accelerometer data collected and temporarily stored prior to the triggering event. Storing such data may be useful where a clinically relevant episode has already passed by the time a triggering event is detected and/or confirmed. In many embodiments, captured accelerometer data includes both recent and prospective accelerometer data. In this way, one or more of a patient's activity levels and body posture before, during, and/or after a triggering event may be combined with other physiological data to prioritize, improve a diagnosis of and/or determine a severity of, a clinically relevant episode, such as an arrhythmia.

Figure 3B:
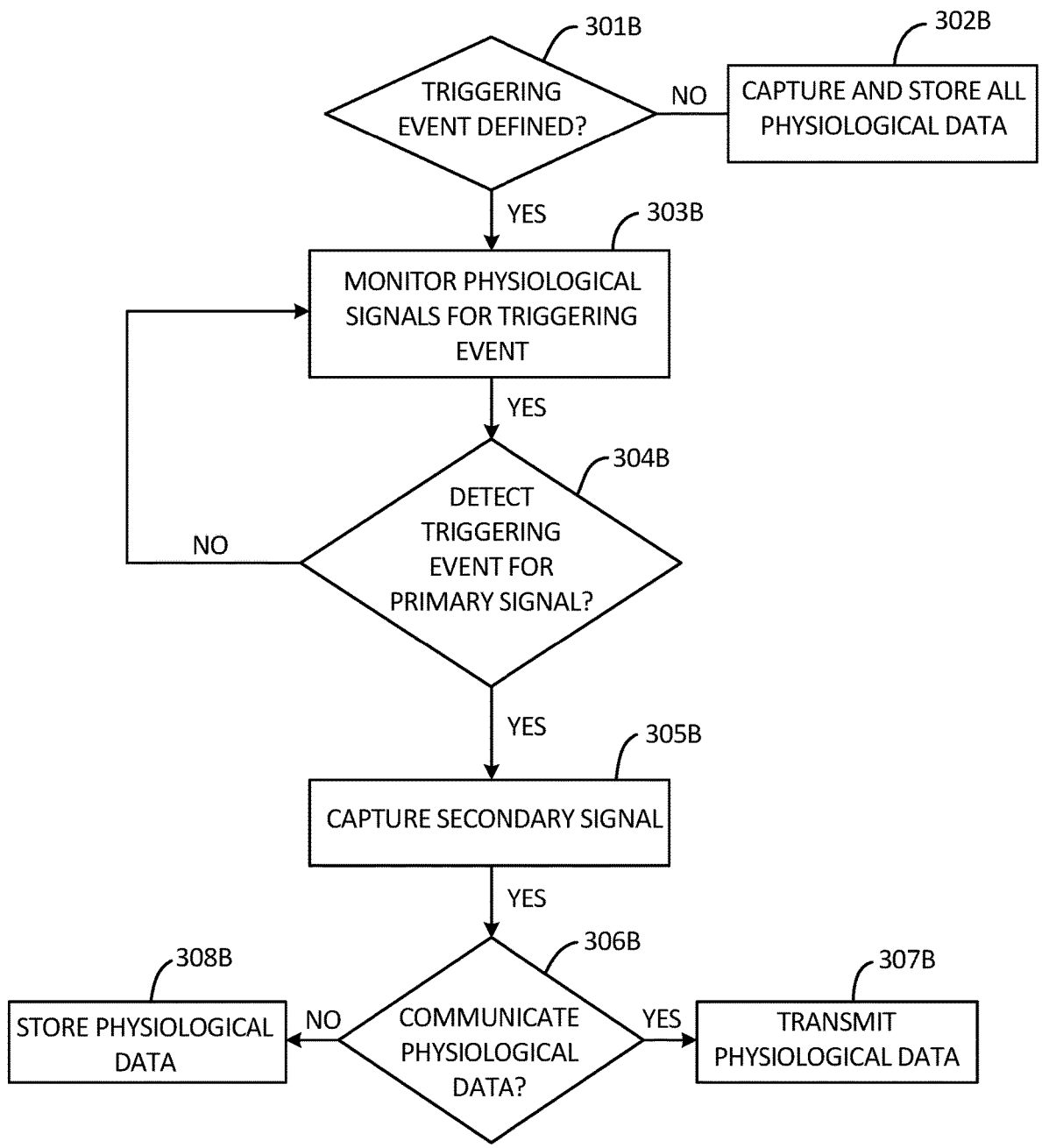

FIG. 3b is a flowchart of a method of monitoring accelerometer signals and other physiological signals, according to an embodiment of the present disclosure. Any of the above embodiments describing methods for sampling and storing accelerometer signals may be utilized here. As shown in FIG. 3b, in addition to accelerometer signals, other physiological signals/data—such as ECG signals/data—may be monitored, captured, stored, and/or communicated to a remote monitoring center in order to permit contextual interpretation. Contextual interpretation improves a diagnosis of an arrhythmia because it permits a medical professional/expert who is reviewing an ECG indicative of an arrhythmia to determine a patient's activity level and posture before, during, and/or after the arrhythmia. For example, a medical professional/expert who is provided with a patient's ECG and the patient's activity level and posture for the same or about the same period of time can determine, among other things, a patient's level of debilitation during and/or after an arrhythmia and a severity level of an arrhythmia to better prioritize one or more arrhythmic episodes. In other words, contextual interpretation enhances a diagnosis of an arrhythmia.

At decision step 301B, the method determines whether a triggering event (discussed in more detail below) is defined. If a triggering event is not defined, the method proceeds to step 302B and captures and stores all physiological data. If a triggering event is defined, the method proceeds to 303B and monitors physiological signals for a triggering event.

At step 302B, all physiological data—e.g., accelerometer data and ECG data—are captured and stored. In many embodiments, accelerometer data and ECG data are continuously and simultaneously monitored, captured, and stored on a medical device. In some embodiments, accelerometer data and ECG data may remain stored on a medical device for future use (e.g., downloaded/transferred at an upcoming appointment). In other embodiments, the accelerometer data and ECG data may be communicated to a remote monitoring center on a continuous and/or periodic basis to permit active (e.g., real-time) or nearly active (e.g., delayed or slightly delayed) monitoring and analysis of the physiological data. The medical professional and/or expert may communicate signals/alerts back to the patient following a review and/or analysis. Although this embodiment is data-intensive and consumes large volumes of memory, this embodiment permits interpretation of a patient's daily electrophysiology with the activities of daily living. In particular, it may be particularly valuable particular diseases and/or conditions and patient health characterizations, among other things. It may also be particularly valuable for interpretation of data in instances where, upon an onset of symptoms, a patient manually triggers capture of physiological data, but an automatically triggered event does not occur.

At step 303B, as discussed above, the method monitors physiological signals (e.g., accelerometer signals and ECG signals) for a triggering event. In comparison to step 302B, step 303B and subsequent steps are less data intensive and that consume less memory may be based on an automatically triggered event.

At decision step 304B, the method determines whether a triggering event has been detected. If no triggering event has been detected, the method returns to step 303B and monitors physiological signals. If a triggering event has been detected, the method captures physiological data. In many embodiments, the triggering event is based on a primary signal (e.g., an ECG signal) and a secondary signal (e.g., an accelerometer signal). In these embodiments, upon detecting a triggering event for a primary signal at decision step 304B, the method proceeds to step 305B and captures a secondary signal.

In one embodiment, for example, the triggering event may be based on a primary signal (e.g., ECG signal) and a secondary signal (e.g., an accelerometer signal). In this embodiment, the primary ECG signal may trigger capture of the secondary accelerometer signal upon detecting automatically triggering events, which are defined and described above in more detail (e.g., upon detecting an arrhythmia, abnormal heart beat, etc.). For example, the primary ECG signal may trigger capture of the secondary accelerometer signal if a patient rate-based or rhythm-based disorder is detected (e.g., tachycardia, bradycardia, atrial fibrillation, and any other arrhythmia). In another example, if a patient experiences a tachycardia episode that triggers the capture of the secondary accelerometer signal, this embodiment may be utilized to determine whether the episode occurred while the patient was sedentary (e.g., a potentially true arrhythmia)

or while the patient was exercising (e.g., a potentially compensated rhythm that may be normal).

In another embodiment, the triggering event may be based on a primary signal (e.g., an accelerometer signal) and a secondary signal (e.g., an ECG signal). In this embodiment, the primary accelerometer signal may trigger capturing of the secondary ECG signal upon detecting a change or significant change in a patient's posture and/or activity level. For example, if the accelerometer detects a change in posture (e.g., a fall), the primary accelerometer signal triggers capture of the secondary ECG signal to determine and/or interpret potential reasons for the patient's change in posture. A benefit of this embodiment is that it provides valuable information relating to syncope episodes and instances in which a patient experiences a fall. Other activity trigger may include one or more of activity intensity, duration, significant changes in activity and/or posture, and abrupt changes in activity and/or posture.

At decision step 306B, the method determines whether to communicate physiological data. For example, the medical device may be programmed or may receive instructions to store and/or communicate captured physiological data. Any of the embodiments discussed herein may be utilized to store and/or communicate physiological data. If physiological data is to be communicated, the method proceeds to step 307B. For example, in some embodiments, the accelerometer data and ECG data may be communicated to a remote monitoring center on a continuous and/or periodic basis to permit active (e.g., real-time) or nearly active (e.g., delayed or slightly delayed) monitoring and analysis of the physiological data. The medical professional and/or expert may communicate signals/alerts back to the patient following a review and/or analysis. If physiological data is not to be communicated, the method proceeds to step 308B and stores the physiological data for future analysis. In these embodiments, accelerometer data and ECG data may remain stored on a medical device for future use (e.g., downloaded/transferred at an upcoming appointment).

Any of the above embodiments described above relating to providing accelerometer data with ECG data to enhance a diagnosis may be programmable. For example, a healthcare provider or medical professional (e.g., physician/expert) may program settings to meet the needs of a particular patient or to follow an adaptive algorithmic approach for auto-programming. In addition, a healthcare provider and/or medical professional may select from or combine the above embodiments in order to reduce consumption of resources necessary for continuously and simultaneously capturing and storing and, in some cases, communicating accelerometer data and ECG data.

Returning to FIG. 3a, at step 303A, patient activity levels and posture are extracted from the sampled accelerometer signal to construct activity profiles. In some embodiments, the sampled accelerometer signal includes activity intensity data from which information relating to a patient's activity levels and posture may be extracted and derived. In many embodiments, step 303A may be performed at a remote monitoring center. For example, the captured and processed accelerometer signals may be communicated (via a cellular or Wi-Fi network, or via Bluetooth connectivity) to a remote monitoring center 106 directly or indirectly through gateway 102. In other embodiments, step 303A may be performed locally (e.g., at adherent device). In some embodiments, step 303A is optional. In one embodiment, because the accelerometer signal is downsampled without utilizing a low-pass filter, both activity level and posture data may be extracted from the downsampled accelerometer signal.

At step 304A, activity profiles are reported with other physiological data associated with a clinically relevant episode. Activity profiles include diagnostically relevant information that may provide insight into various clinically relevant episodes. In many embodiments, activity profiles including patient activity level and posture are reported with arrhythmias to prioritize arrhythmias, improve a diagnosis of an arrhythmia (e.g., provide a standardized way of quantifying and presenting activity information), determine a severity of an arrhythmia, and/or determine a level of debilitation associated with an arrhythmias. In some embodiments, in a case of bradycardia, an activity profile showing a patient to be active before and/or after the bradycardia episode may suggest chronotropic incompetence. In other embodiments, a case of tachycardia, an activity profile showing a patient at rest before and/or after the tachycardia episode may be indicative of heart failure (HF) worsening. In some embodiments, step 304A is optional.

Table 1 is an example of an arrhythmia report for clinician review in which detected arrhythmias are reported based on a priority (e.g., diagnostic relevance) and/or a severity of a detected arrhythmia, according to an embodiment of the present disclosure. The arrhythmias reported in Table 1 were captured over a period of a month and prioritized in a report based on arrhythmia severity. The priority assigned to a given episode was based on patient activity and posture information (e.g., via an activity profile) derived from an accelerometer. As shown in Table 1, the first column reports the day and time of the episode, the rhythm column reports the type of arrhythmia episode detected, and the activity column reports whether the patient was at rest or active during the arrhythmia episode.

TABLE 1

Prioritized Arrhythmia Report Based on Activity and Posture

| Day/Time | Rhythm | Activity |
| --- | --- | --- |
| Day 24/04:15:00 | wide-complex tachycardia | at rest |
| Day 6/10:30:00 | sinus tachycardia | at rest |
| Day 2/11:00:00 | sinus tachycardia | active |
| Day 2/14:00:00 | sinus tachycardia | active |

As reported in Table 1, the wide-complex tachycardia episode while the patient was at rest is identified as the most diagnostically relevant, followed by the sinus tachycardia episode while the patient was at rest. The two sinus tachycardia episodes while the patient was active were reported as being the least diagnostically relevant among these detected arrhythmias. Because tachycardia events are less likely to be identified with respect to a patient at rest, the wide-complex tachycardia and sinus tachycardia are given a higher significance than the tachycardia events identified while the patient is active. In other embodiments, the determination of whether the patient is at rest or active may have a different impact on the prioritization of the episode. For example, a bradycardia episode detected while a patient is active may be given higher priority than a bradycardia episode detected while a patient is at rest. In this way, arrhythmias (e.g., tachycardias) may be prioritized based on patient activity information to promote prompt notification of resting tachycardia episodes.

For example, FIGS. 4a-4d and 5a-5e are graphical views of activity profiles of a patient during tachycardia episodes and bradycardia episodes, respectively, according to an embodiment of the present disclosure. As shown in FIGS.

4a-4d and 5a-5e, activity levels are plotted with time. The activity levels, represented as horizontal dashed lines, include moderate activity, light activity, and sedentary. In addition, the vertical dashed line indicates an arrhythmia occurrence time, the solid line indicates raw activity intensity data about 30 minutes before and about 5 to 7 minutes after the arrhythmia, and the shaded areas indicate durations when the patient was deemed active based on activity intensity.

Figure 4A:
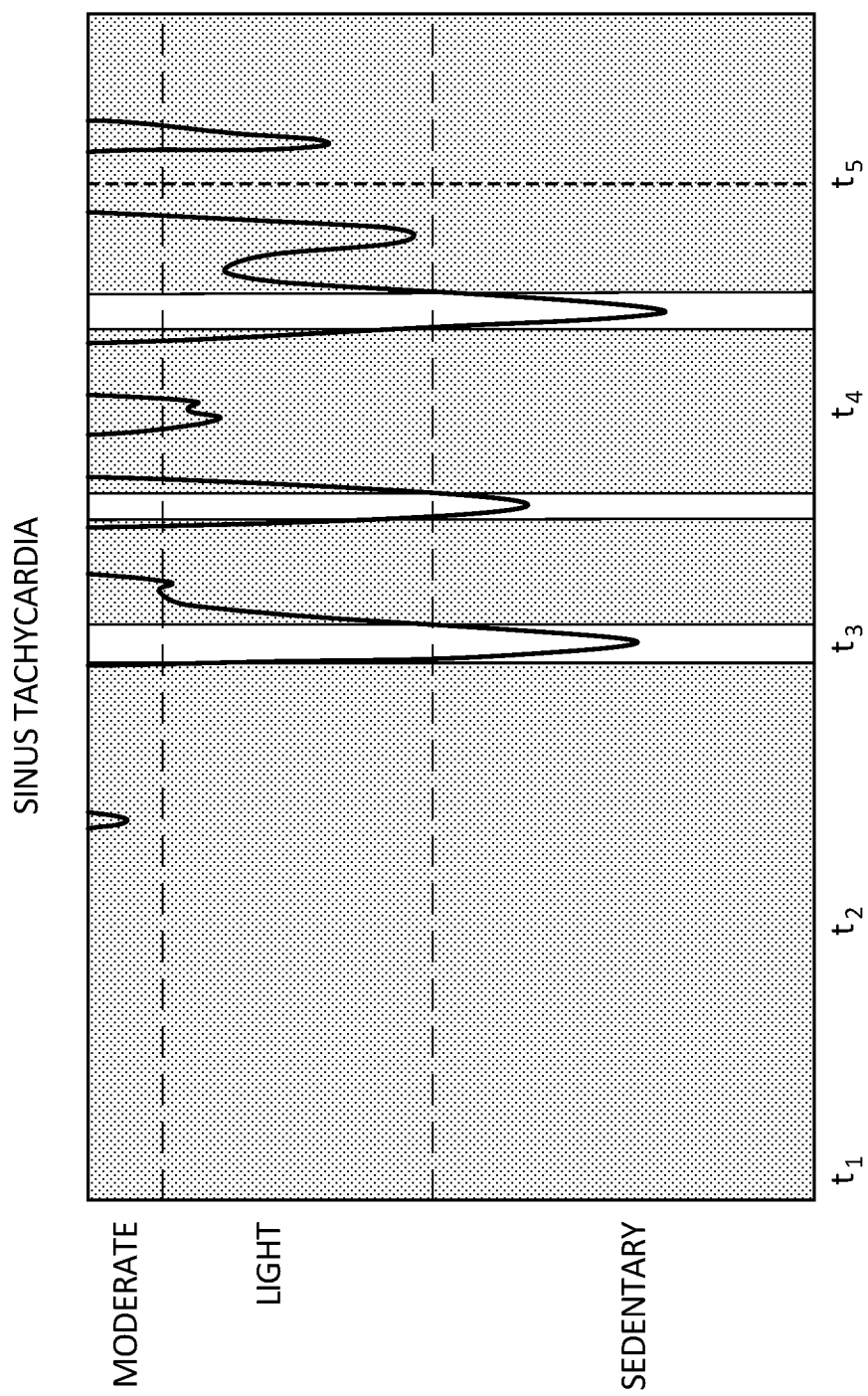
FIGS. 4a-4d are graphical views of activity intensities and time-course of patients during tachycardia episodes, according to one or more embodiments of the present disclosure.
Figure 4B:
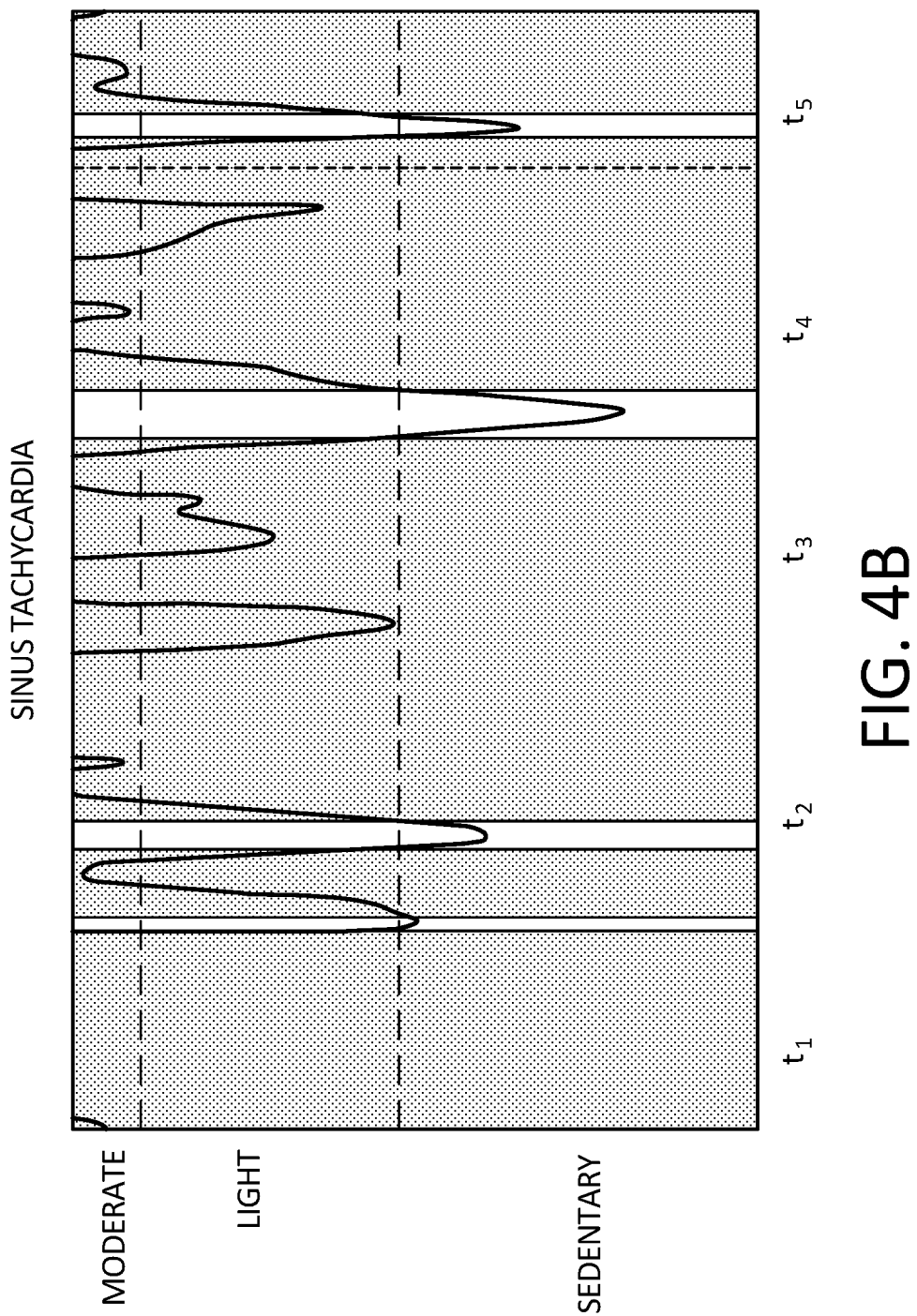
Figure 4C:
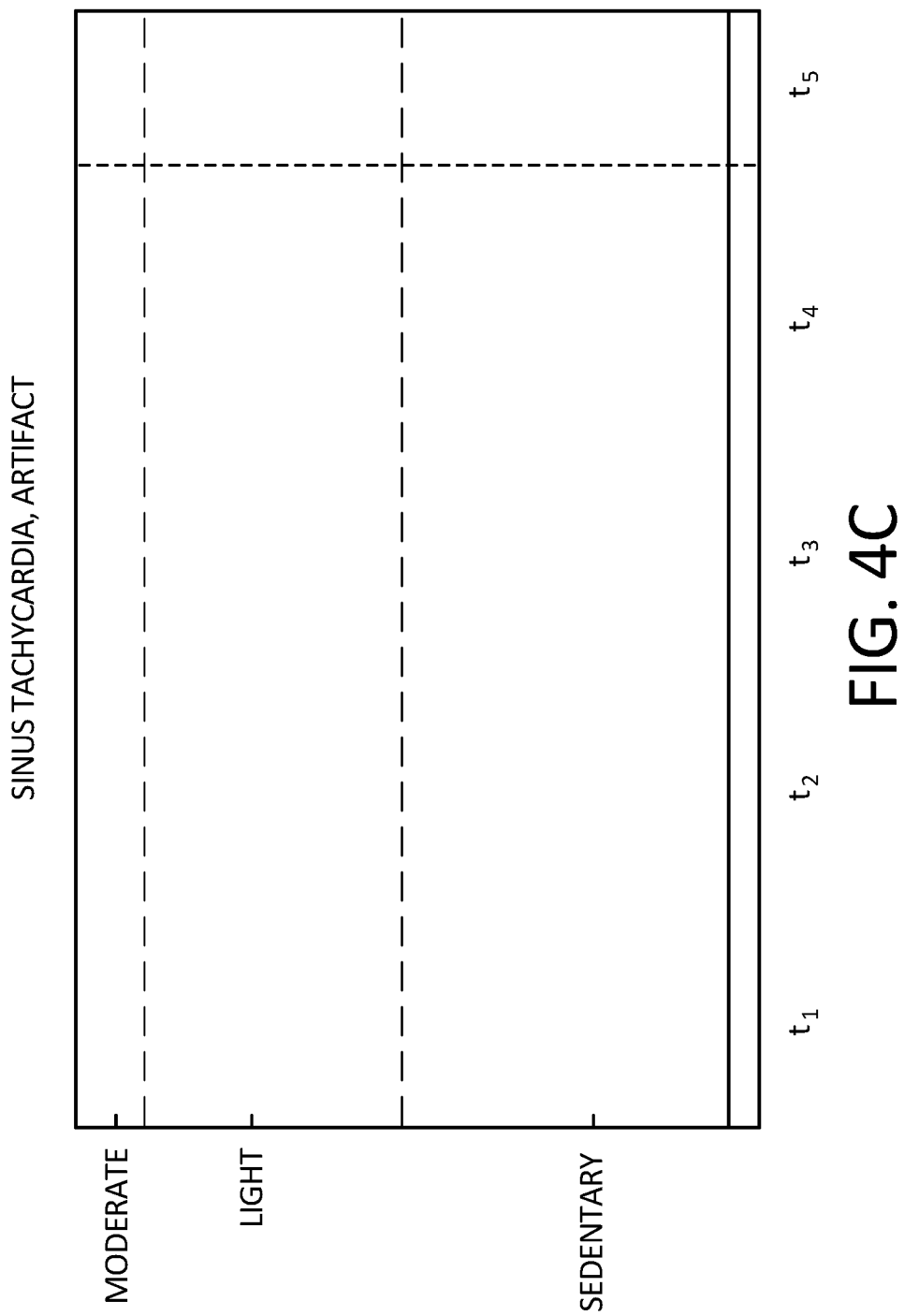
Figure 4D:
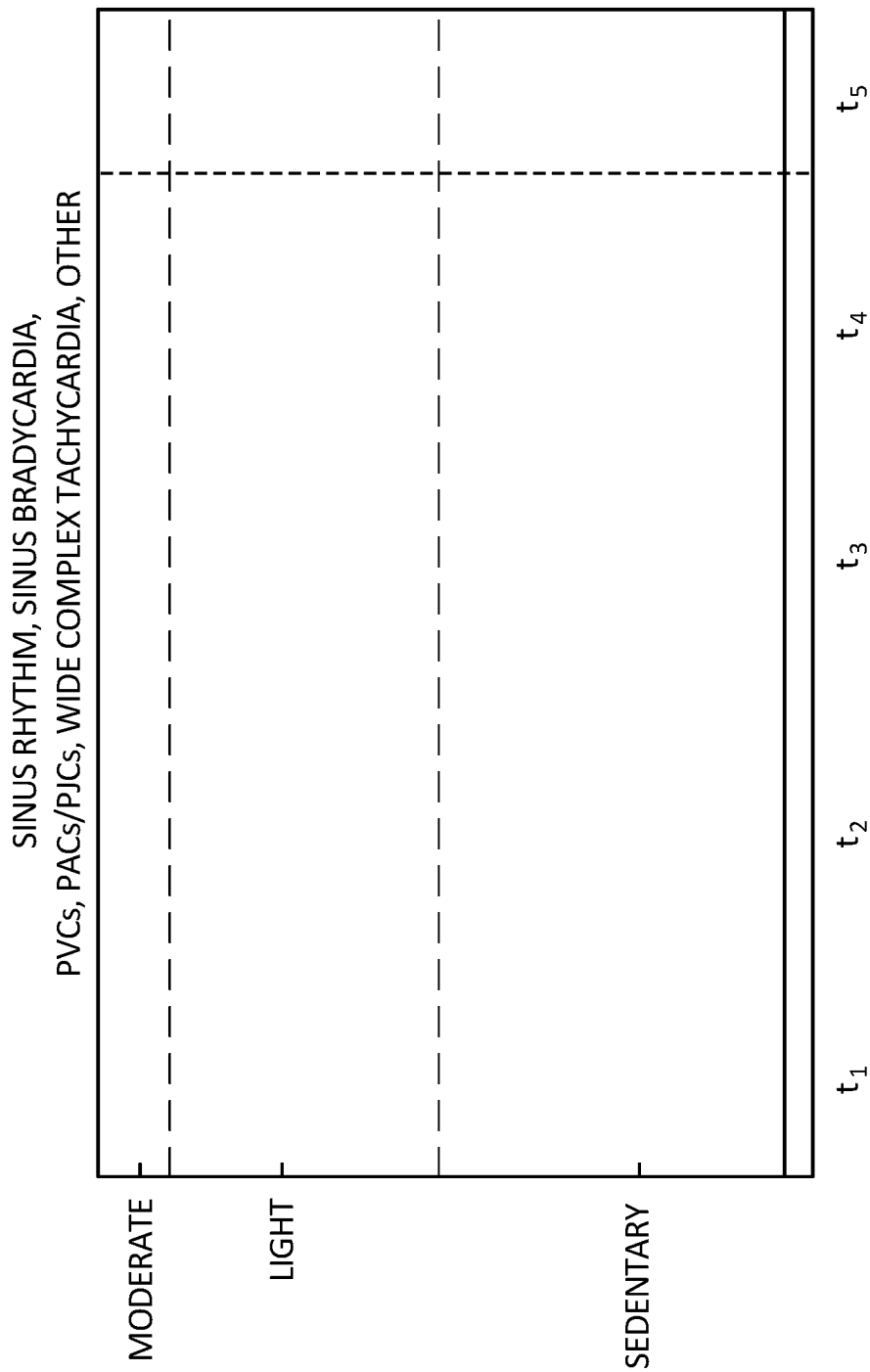

FIGS. 4a-4d illustrate an embodiment relating to tachycardia episodes in which activity profiles may be utilized to determine a severity of detected arrhythmias and to prioritize a reporting of the detected arrhythmias. Each of FIGS. 4a and 4b show two sinus tachycardia events around $t_5$, in which the patient was active before and after the tachycardia episode. FIGS. 4c and 4d show a resting sinus tachycardia event between $t_4$ and $t_5$ and a wide-complex tachycardia event between $t_4$ and $t_5$, respectively, in which the patient activity profile shows no activity before and after the tachycardia episode. According to this embodiment, the wide-complex tachycardia episode of FIG. 4d, having occurred while the patient was at rest, would be the most severe and reported first. Next would include the resting sinus tachycardia episode of FIG. 4c, followed by the two sinus tachycardia episodes of FIGS. 4a and 4b. In this way, activity information derived from the high frequency components of the monitored accelerometer signal are utilized to determine the severity of detected arrhythmias.

Figure 5A:
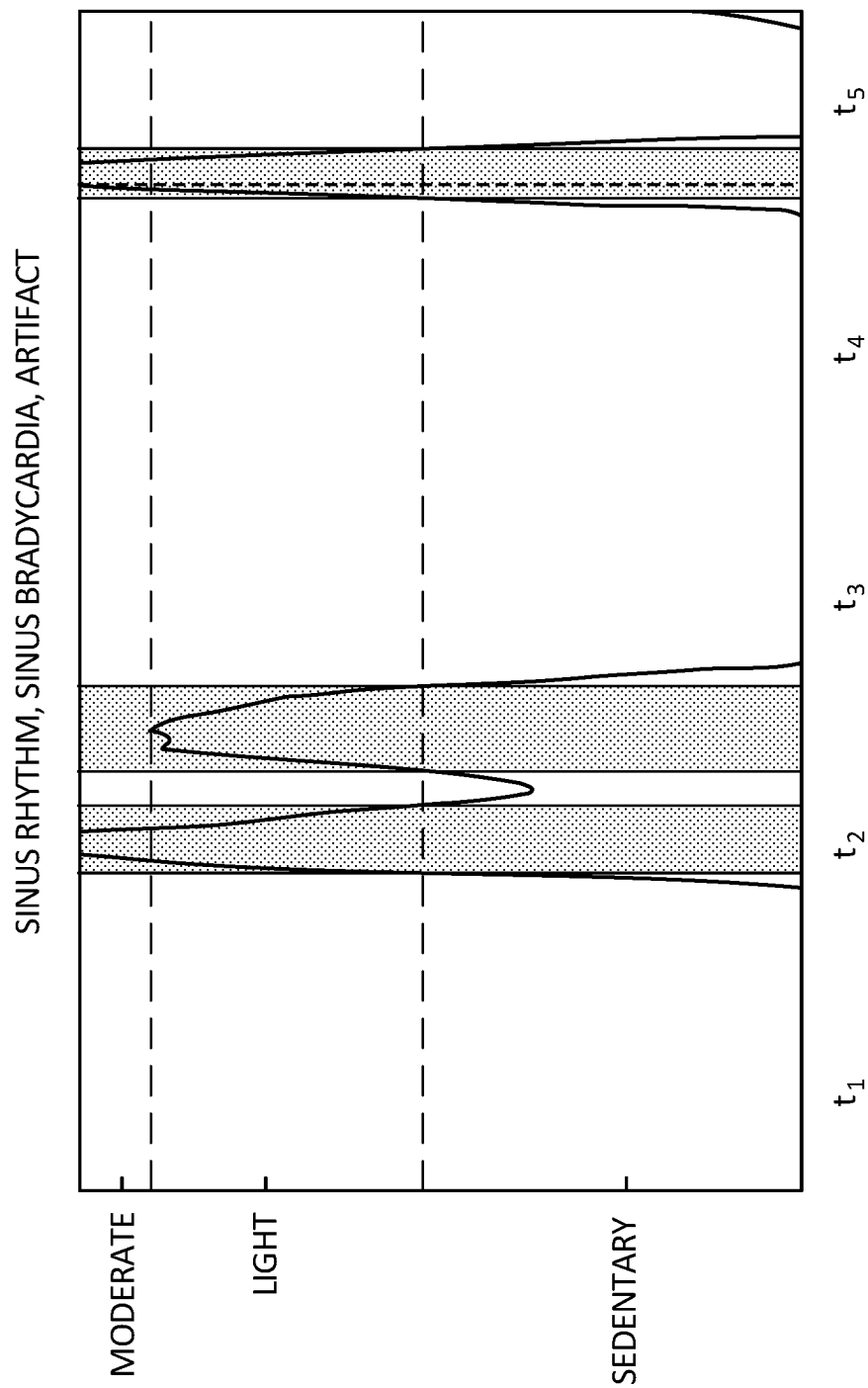
FIGS. 5a-5e are graphical views of activity intensities of patients during bradycardia episodes, according to one or more embodiments of the present disclosure.
Figure 5B:
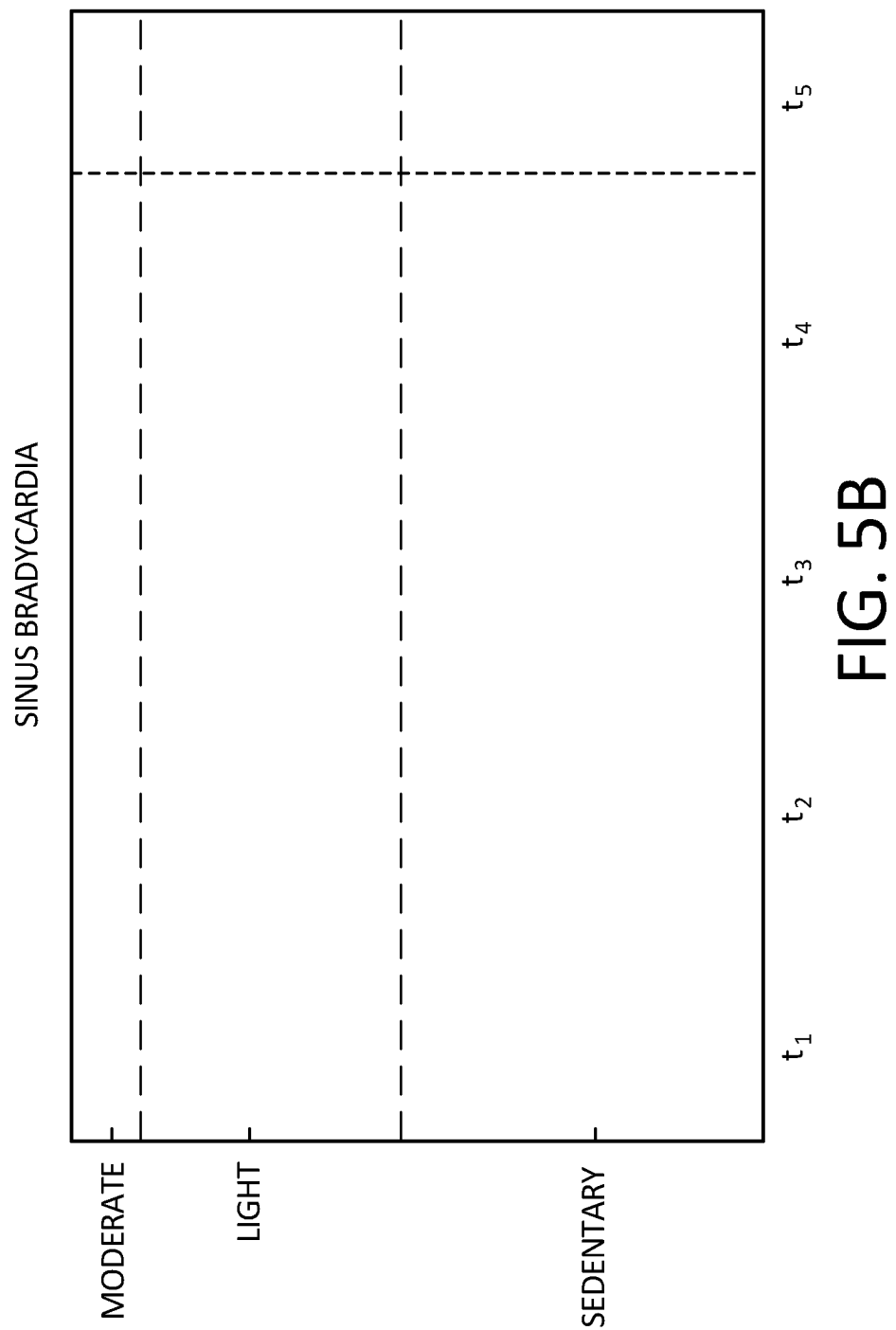
Figure 5C:
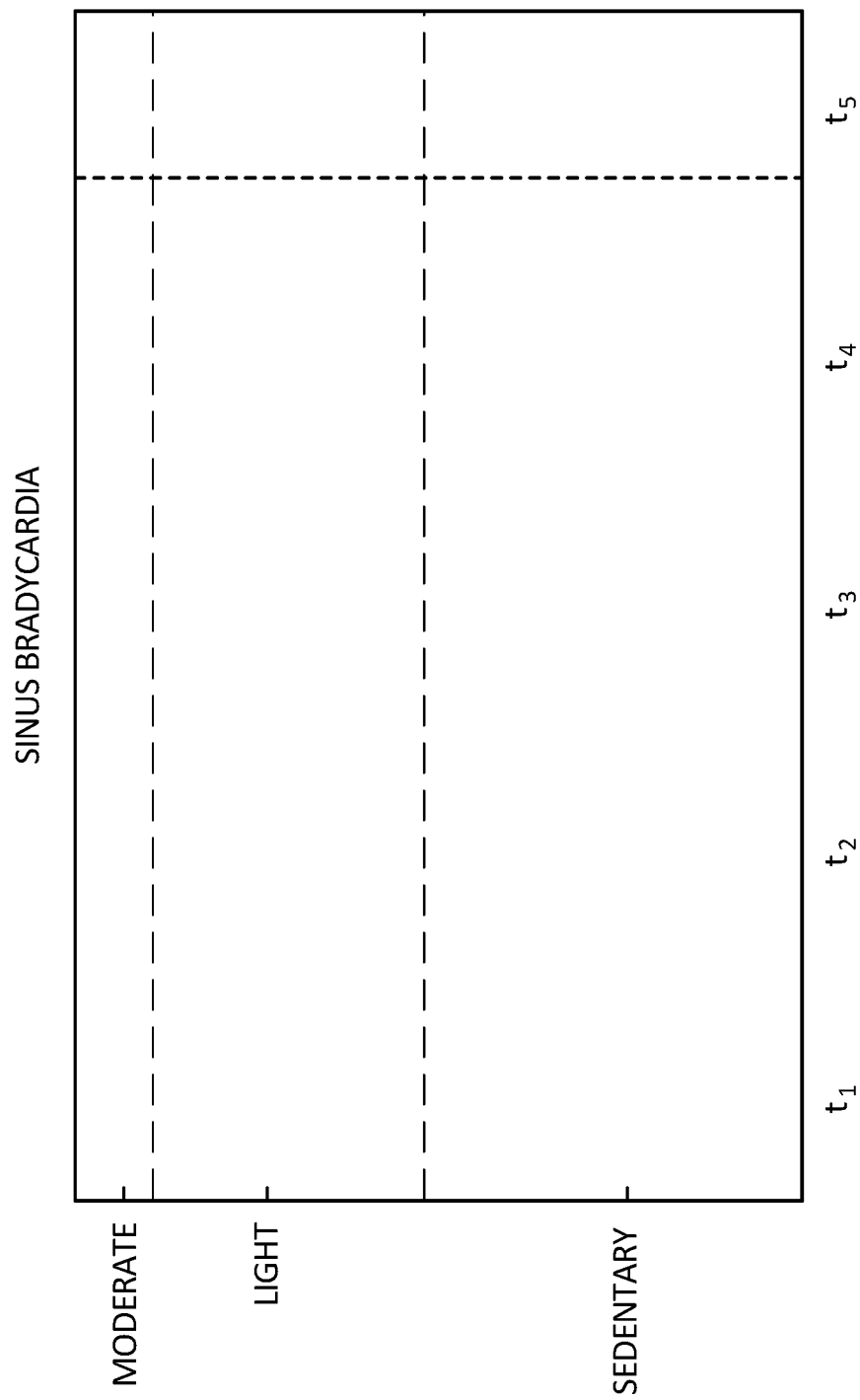
Figure 5D:
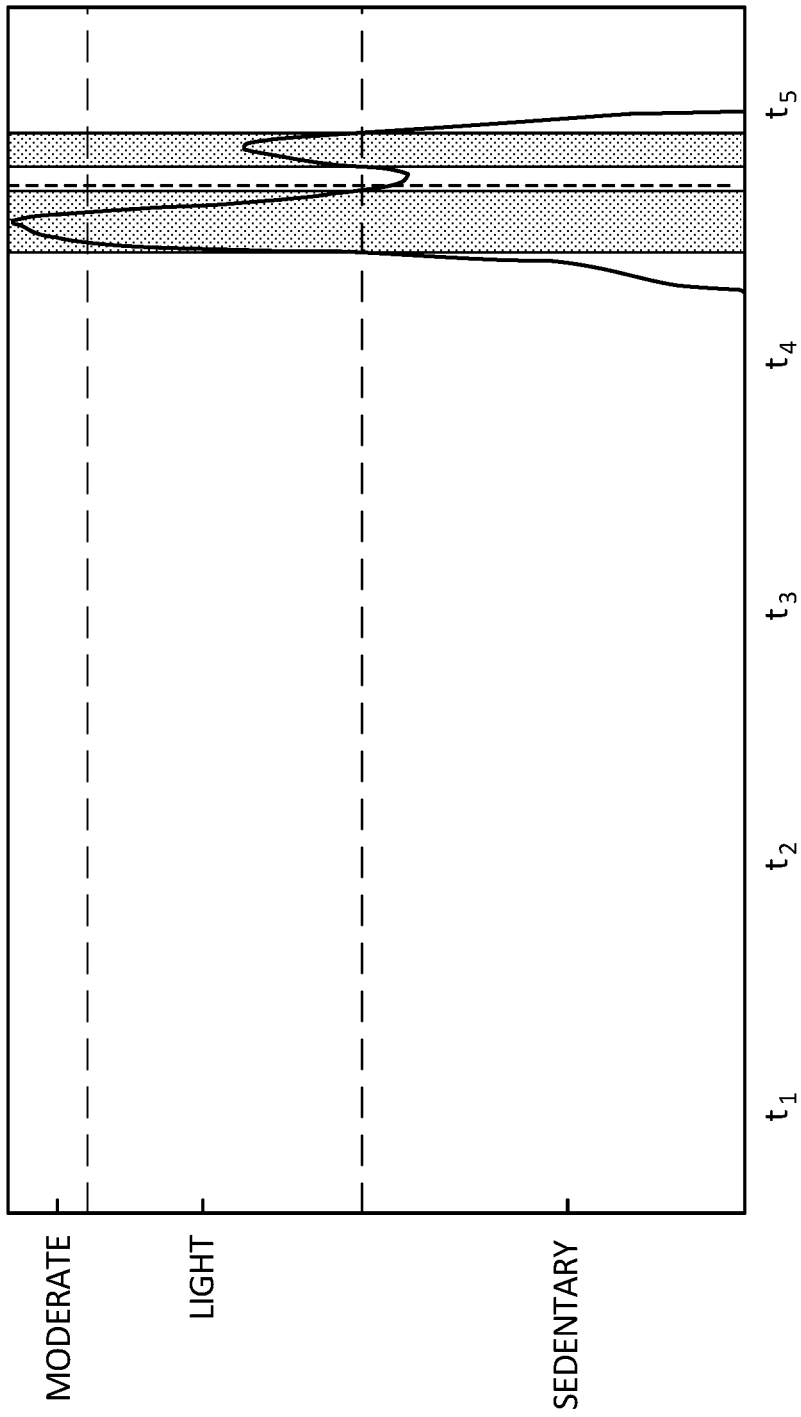
Figure 5E:
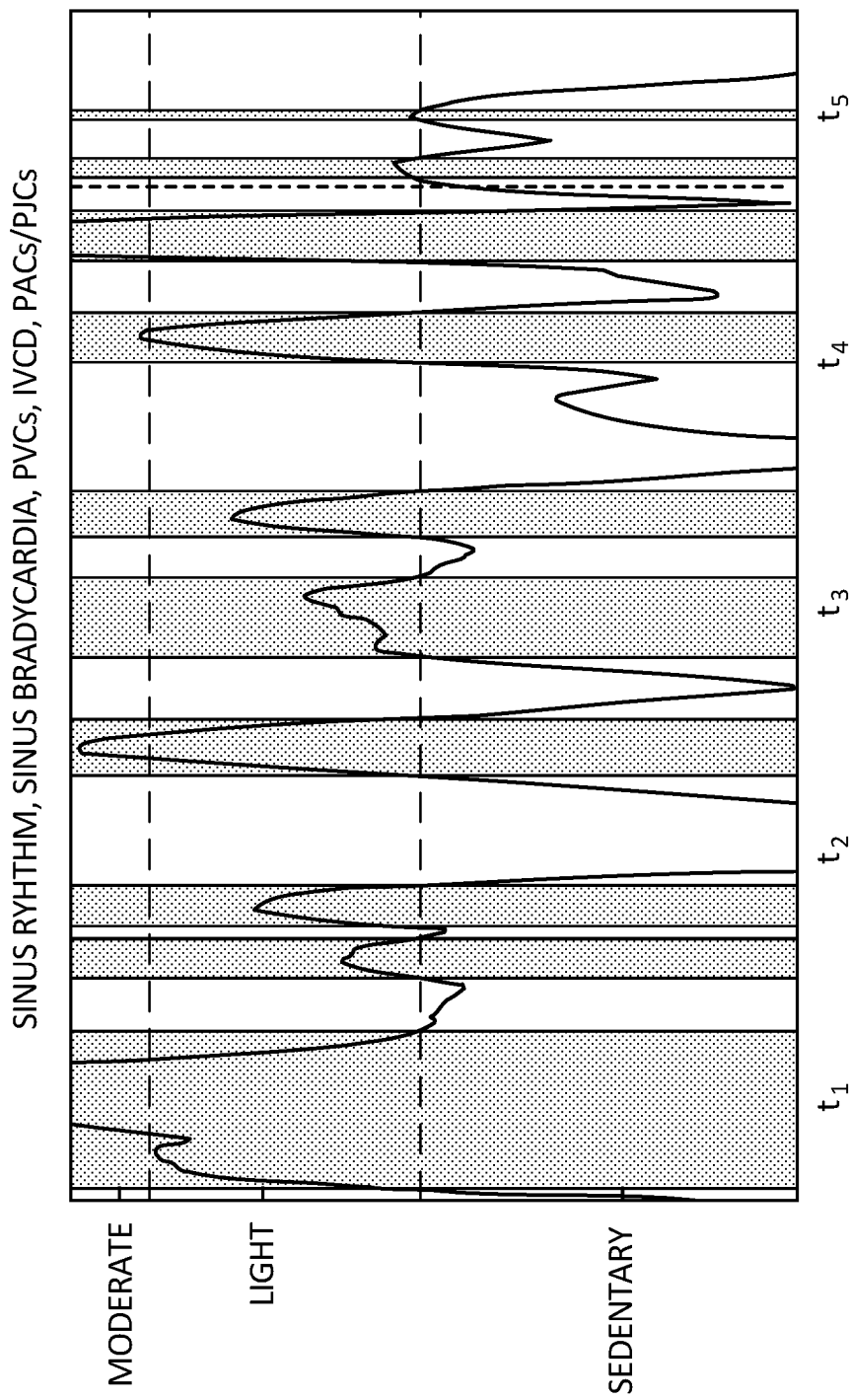

FIGS. 5a-5e illustrate an embodiment relating to bradycardia episodes in which activity profiles may be utilized to determine a severity of detected arrhythmias and to prioritize a reporting of the detected arrhythmias. As shown in FIGS. 5a-5e, the patient was monitored over a 12-day period, with 1 sinus bradycardia episodes detected between $t_4$ and $t_5$ on a first day (FIG. 5a); 3 episodes between $t_4$ and $t_5$ on a second day (FIGS. 5b-5d); and between $t_4$ and $t_5$ on a last day (FIG. 5e). According to the activity profiles, the patient was active during the bradycardia episodes reported in FIGS. 5a, 5d, and 5e, whereas the patient was at rest during the bradycardia episodes reported in FIG. 5b and FIG. 5c. Based on the activity profile and arrhythmia severity, the bradycardia event reported in FIG. 5e may indicate chronotropic incompetence since the patient was moderately to highly active. The other bradycardia events associated with activity at night could be indicative of posture-related syncope.

In addition to being used to prioritize a reporting of the detected arrhythmias, the information provided in FIGS. 4a-4d and 5a-5e may also be used to triage a severity of patient conditions. For example, in some embodiments, a monitoring center (e.g., healthcare clinic, hospital, etc.) may receive physiological data (e.g., accelerometer and/or ECG data) from two or more patients. The data provided in FIGS. 4a-4d and 5a-5e, for example, may be utilized by medical professionals/experts (e.g., triage nurses, physicians, experts, etc.) to assess and/or prioritize whether data must be urgently processed, to aid in emergency response management and resource management, and to prioritize two or more patients based on severity.

Figure 6A:
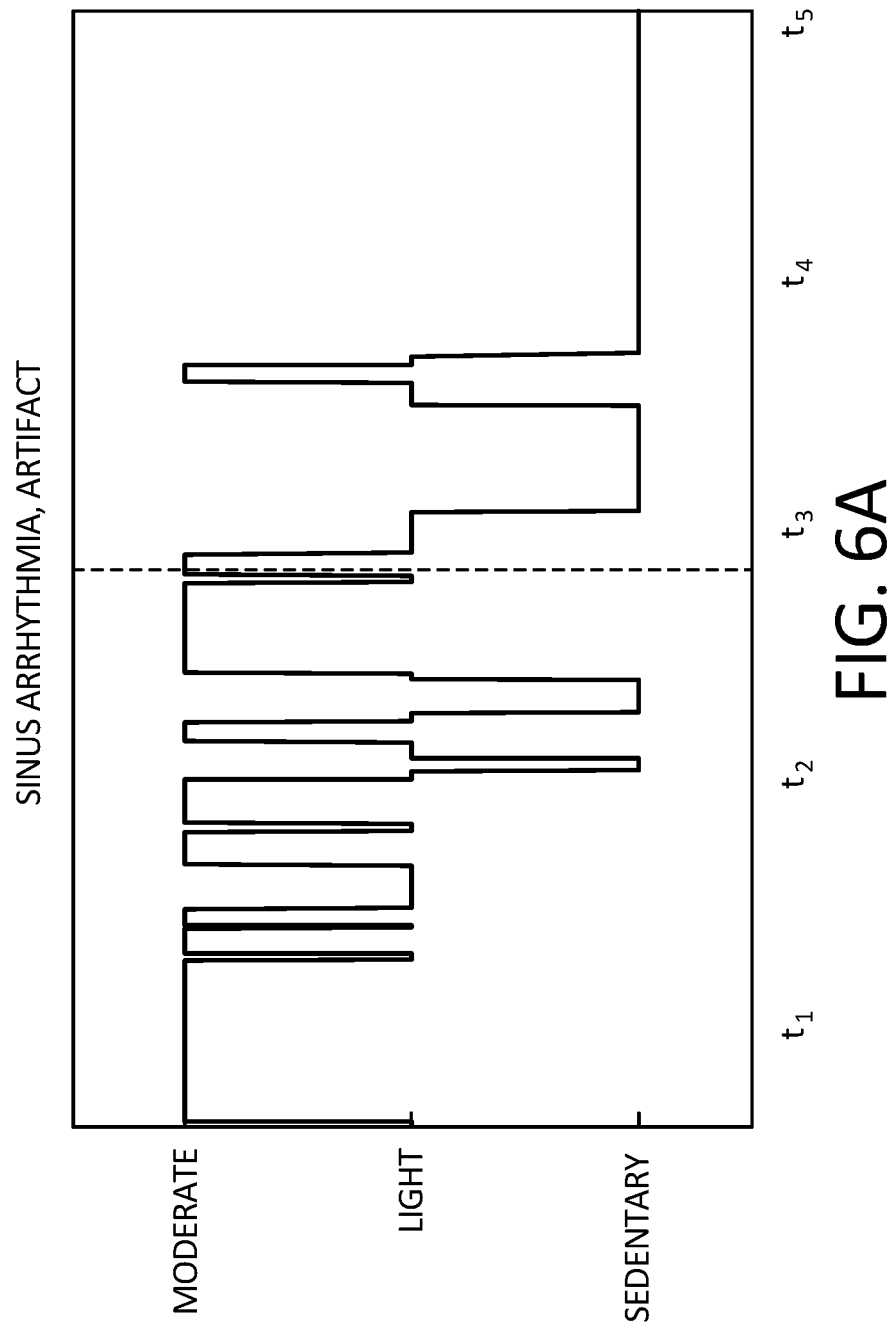
FIGS. 6a-6b are graphical views of activity profiles of two patients before and after each patient's arrhythmic episode, according to one or more embodiments of the present disclosure.
Figure 6B:
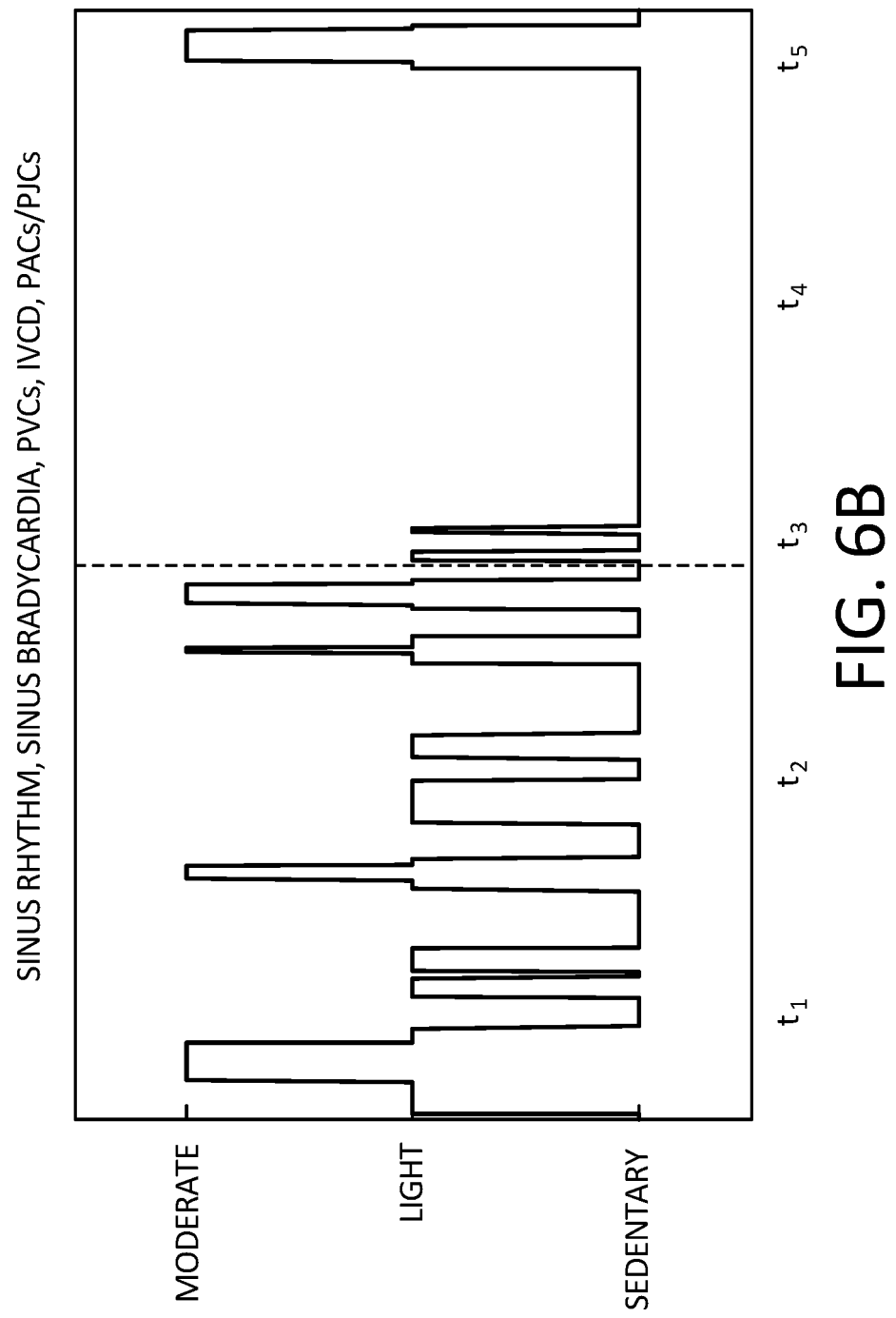

FIGS. 6a-6b are graphical views of activity profiles of two different patients about 30 minutes before and about 30 minutes after each patient's arrhythmic episodes, according to an embodiment of the present disclosure. The solid line plots activity levels (e.g., sedentary, moderate, light) with time. The vertical dashed line indicates a time of arrhythmia occurrence. From these activity profiles, a level or degree of debilitation of a patient may be determined via changes in a patient's activity level before and after an arrhythmia occurrence. In particular, FIGS. 6a and 6b both show a patient being active before the sinus arrhythmia and bradycardia, but who became mostly sedentary after the sinus arrhythmia and bradycardia, respectively.

Figure 7A:
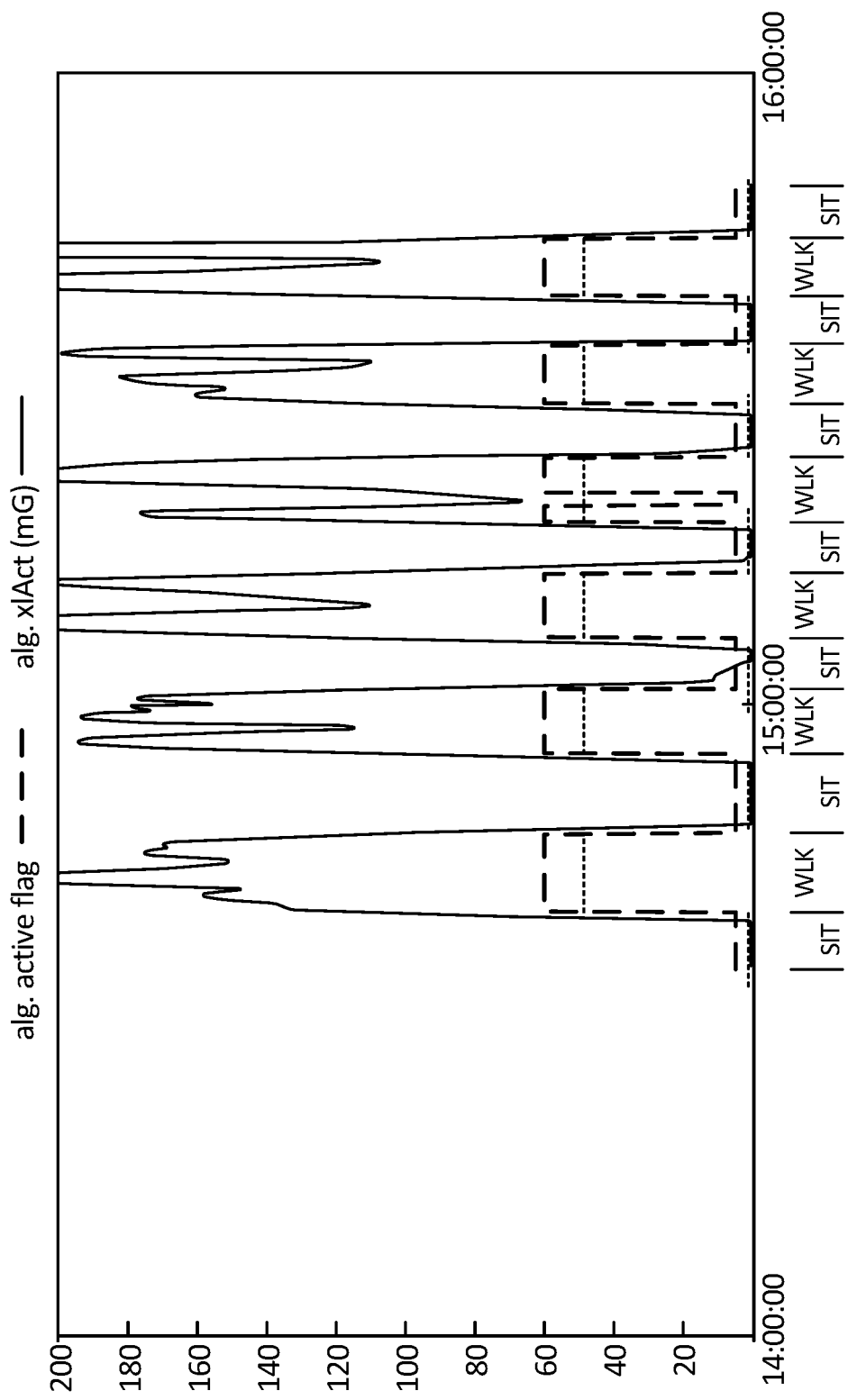
FIGS. 7a-7b are graphical views of activity profiles and intensities of two patients alternating between walking and resting, according to one or more embodiments of the present disclosure.
Figure 7B:
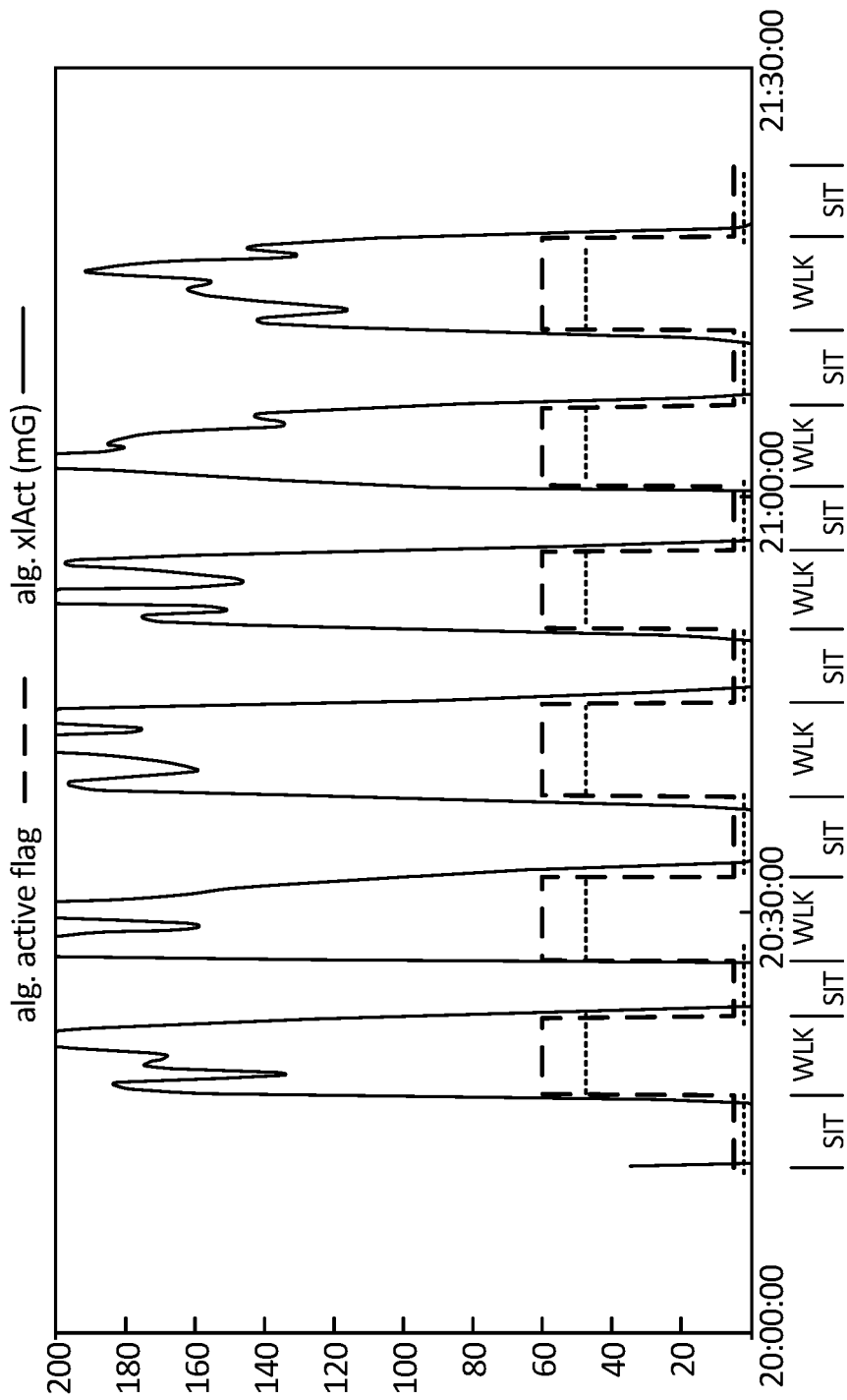

FIGS. 7a-7b are graphical views of activity profiles of two different patients alternating between walking and resting, according to an embodiment of the present disclosure. In particular, FIGS. 7a and 7b provide examples of a study in which a patient alternated between walking and resting. The short-dashed lines indicate activity types as derived from activity logs, the long-dashed lines are the active versus rest detection, and the solid line is the activity intensity in mG as derived via the methods described above with respect to FIG. 3. As shown in FIGS. 7a and 7b, the amount of data required to accurately construct an activity profile is reduced via the methods of the present disclosure with respect to FIG. 3, while ensuring that patient activity and posture may be continuously tracked and that patient activity instances as short as a 4-minute walk and/or activity durations may be accurately detected.

Figure 8:
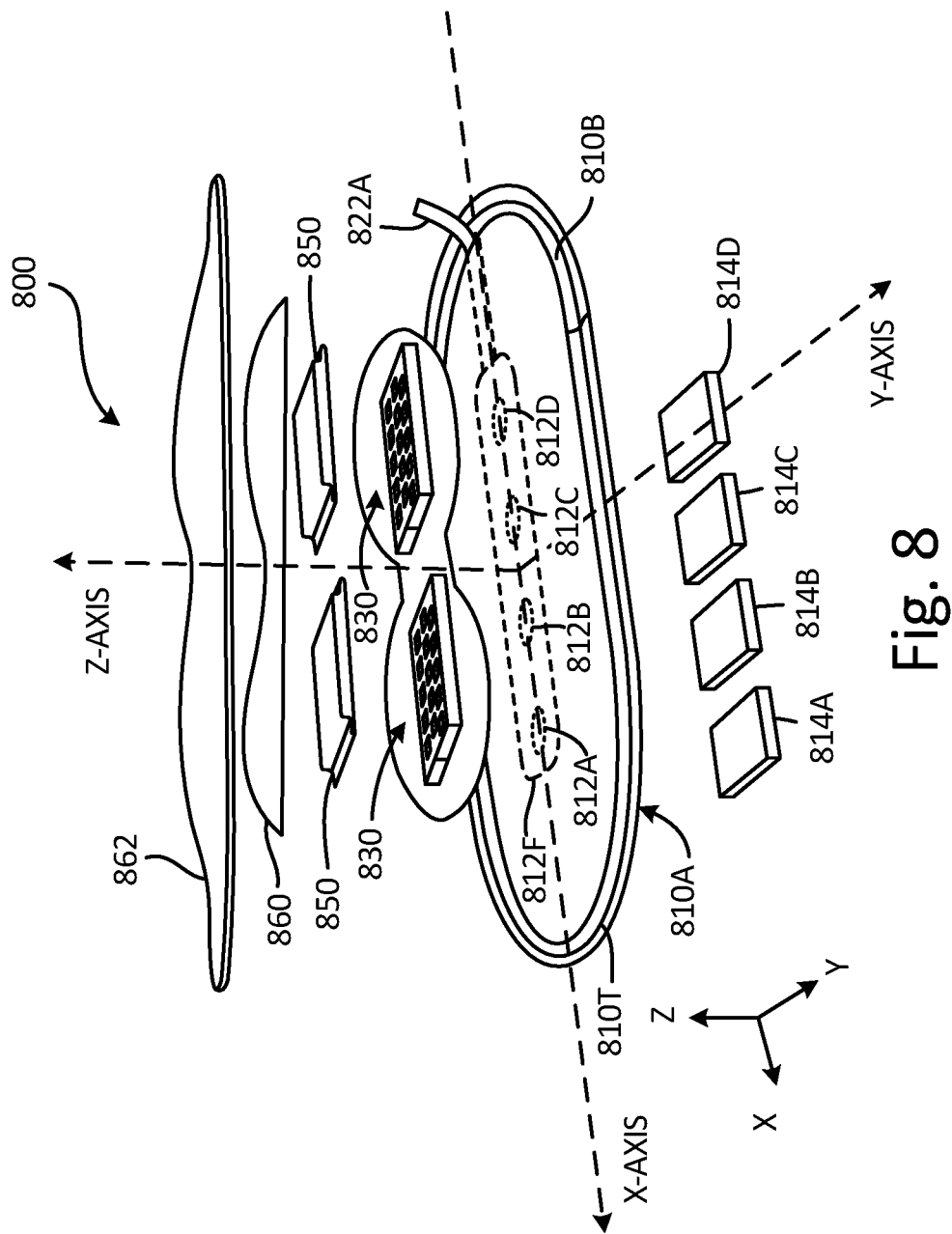
FIG. 8 is a schematic diagram of an adherent device, according to one or more embodiments of the present disclosure.

FIG. 8 is an exploded view, respectively, of a patient medical device 800, according to an embodiment of the present disclosure. In the embodiment shown in FIG. 8, patient medical device 800 is an adherent device, but as described above may also be implemented as an implantable device, an injectable device, or similar wearable device. In the embodiment shown in FIG. 8, adherent device 800 includes adherent tape 810T, electrodes 812A, 812B, 812C, 812D with gels 814A, 814B, 814C, 814D, printed circuit board (PCB) 820, flexible connector 822A, electrical components/sensors 830 mounted on PCB 820, batteries 850, electronics housing cover 860, and flexible cover 862.

Adherent device 800 comprises an accelerometer and at least two electrodes—although the embodiment shown in FIG. 8 includes electrodes 812A, 812B, 812C and 812D. Adherent device 800 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 800 comprises a first side, or a lower side 810A, that is oriented toward the skin of the patient when placed on the patient. The adherent patch 800 may also comprise a tape 810T, which is a material, preferably breathable, with an adhesive (not shown) to adhere to patient P. Electrodes 812A, 812B, 812C and 812D are affixed to adherent patch 800. In many embodiments, at least four electrodes are attached to the patch. Gels 814A, 814B, 814C and 814D can each be positioned over electrodes 812A, 812B, 812C and 812D, respectively, to provide electrical conductivity between the electrodes and the skin of the patient. Adherent patch 800 also comprises a second side, or upper side 810B. In many embodiments, electrodes 812A, 812B, 812C and 812D extend from lower side 810A through adherent patch 100 to upper side 810B. An adhesive can be applied to upper side 810B to adhere structures, for example a breathable cover, to the patch such that the patch can support the electronics and other structures when the patch is adhered to the patient. In many embodiments, adherent patch 100 may comprise a layer of breathable tape 810T, for example a tricot-knit polyester fabric, to allow moisture vapor and air to circulate to and from the skin of the patient through the tape. Electrical signals received at electrodes 812A-812D may be communicated to electronic components 830 via flexible connection 822A, which is connected to a PCB (not shown). Cover 860 is positioned over batteries 850 and electronic components 830 to provide protection for both. In addition, flexible cover 862 is positioned to encase the flexible PCB 820, electronics components 830, and/or adherent patch 810 so as to protect at least the electronics components and the PCB Electronic components 830 may include an accelerometer configured to measure an activity and posture of a patient. In particular, the accelerometer may include an activity sensor and/or activity circuitry for monitoring, capturing, and processing accelerometer signals, as well as extracting patient activity and posture information and report activity profiles. In many embodiments, the accelerometer may further include an analog-to-digital converter and/or a processor for sampling accelerometer signals at non-regular timing intervals (e.g., a timing jitter) and/or for sampling signals at one or more of a first sampling rate, a second sampling rate, and a reduced sampling rate. The accelerometer may include a three-axis accelerometer, such as the one described above. The accelerometer may include an x-axis, a y-axis, and a z-axis, each of which may be sensitivity to gravity such that the orientation of the patient and/or accelerometer may be determined in relation to gravity. As shown above with respect to FIG. 1, the three axes of the three-axis accelerometer may be aligned with one or more of the patient coordinate system 100P and the 3D coordinate reference system 112XYZ.

In addition, electronic components 830 may include ECG circuitry utilized to generate electrocardiogram signals and data from two or more of electrodes 812A, 812B, 812C and 812D in many ways. In some embodiments, ECG circuitry (not shown) is connected to inner electrodes 812B and 812C, which may comprise sense electrodes of the impedance circuitry as described above. In many embodiments, the ECG circuitry may measure the ECG signal from electrodes 812A and 812D when current is not passed through electrodes 812A and 812D. In addition, electronic components 830 may include bioimpedance circuitry connected to two or more of electrodes 812A, 812B, 812C and 812D to allow electronic components 830 to measure a bioimpedance associated with the patient.

In addition, electronic circuitry 830 may comprise a processor module that can be configured to analyze physiological parameters monitored by adherent device 800 and to control collection and transmission of data from the electrocardiogram circuitry. In one embodiment, the processor module included as part of electronic circuitry 830 comprises a tangible medium, for example read only memory (ROM), electrically erasable programmable read only memory (EEPROM) and/or random access memory (RAM). Tangible medium may, for example, store one or more of threshold levels, population-based baseline data, patient-specific baseline data, recently monitored physiological data, and previously captured physiological data, as discussed above. Processing of monitored physiological parameters such as accelerometer signals and/or ECG signals may be distributed between the local processor module included as part of electronic circuitry 830 and remote monitoring system 106 (shown in FIG. 1).

In one embodiment, a processor and/or a processing module include electronic circuitry configured to monitor accelerometer signals and/or ECG signals of a patient; capture and process accelerometer signals at a reduced sampling rate and at non-regular intervals, as well as ECG segments, in response to triggering events; extract patient activity and posture information from the captured and processed accelerometer signal; and/or report activity profiles with patient activity and posture information. The processor and/or processing module may also communicate and/or transmit accelerometer signals/data, ECG signals, and/or captured ECG segments to a remote monitoring center for review by an analysis.

Figure 9:
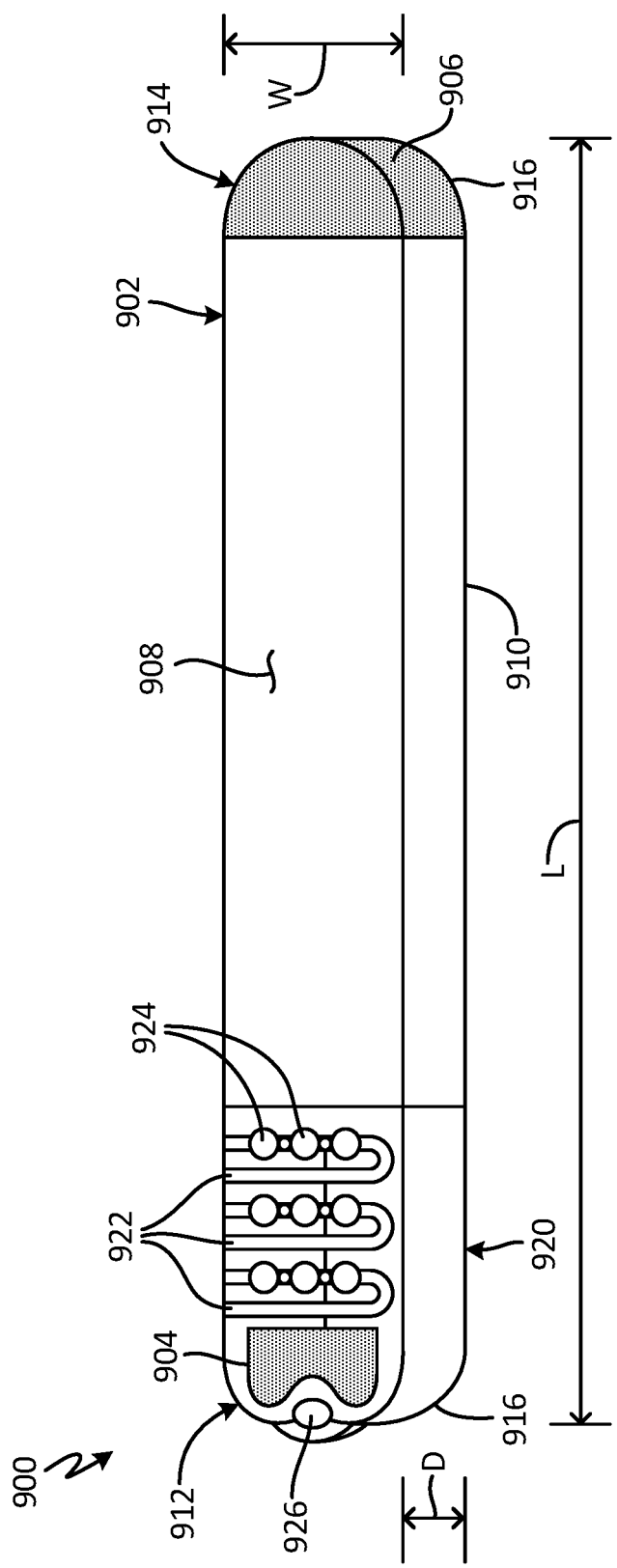
FIG. 9 is a schematic diagram of an insertable device, according to one or more embodiments of the present disclosure.

In many embodiments, electronics components 830 comprise wireless communications circuitry (not shown) to communicate with remote center 106. The PCB (not shown) may comprise an antenna to facilitate wireless communication. The antenna may be integral with the PCB or may be separately coupled thereto. The wireless communication circuitry can be coupled to the accelerometer and/or electrocardiogram circuitry to transmit to a remote center with a communication protocol at least one of the accelerometer signals, electrocardiogram signals, or other features collected by the adherent device 800. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two-way protocol such that the remote center is capable of issuing commands to control data collection. For example, in one embodiment a HCP may push updated sampling rates, timing jitters, and/or urgent notifications to adherent device 800. For example, a sampling rate may be increased and/or decreased, or a timing jitter may be altered, to improve a quality of data being collected. In addition, an urgent notification may be pushed to a patient to alert patient that urgent medical attention may be necessary. C FIG. 9 is a perspective view of an insertable monitoring device 900 according to an embodiment of the present invention. In the embodiment shown in FIG. 9, insertable cardiac monitor 900 is defined by a length L, a width W and thickness or depth D and is in the form of an elongated rectangular prism wherein the length L is much larger than the width W, which in turn is larger than the depth D. In one embodiment, the geometry of the insertable cardiac monitor 900—in particular a width W greater than the depth D—is selected to allow the cardiac monitor 900 to be inserted under the skin of the patient using a minimally invasive procedure and to remain in the desired orientation during insert. For example, the device shown in FIG. 9 includes radial asymmetries (notably, the rectangular shape) along the longitudinal axis that maintains the device in the proper orientation following insertion. For example, in one embodiment the spacing between proximal electrode 904 and distal electrode 906 may range from 30 millimeters (mm) to 55 mm, 35 mm to 55 mm, and from 40 mm to 55 mm and may be any range or individual spacing from 25 mm to 60 mm. In addition, insertable cardiac monitor 900 may have a length L that ranges from 30 mm to about 70 mm. In other embodiments, the length L may range from 40 mm to 60 mm, 45 mm to 60 mm and may be any length or range of lengths between about 30 mm and about 70 mm. In addition, the width W of major surface 908 may range from 3 mm to 10 mm and may be any single or range of widths between 3 mm and 10 mm. The thickness of depth D of cardiac monitor device 900 may range from 2 mm to 9 mm. In other embodiments, the depth D of insertable cardiac monitor 900 may range from 2 mm to 5 mm and may be any single or range of depths from 2 mm to 9 mm. In addition, insertable cardiac monitor 900 according to an embodiment of the present invention is has a geometry and size designed for ease of implant and patient comfort. Embodiments of insertable cardiac monitor 900 described in this disclosure may have a volume of three cubic centimeters (cm) or less, 1.5 cubic cm or less or any volume between three and 1.5 cubic centimeters.

In the embodiment shown in FIG. 9, once inserted within the patient, the first major surface 908 faces outward, toward the skin of the patient while the second major surface 910 is located opposite the first major surface 908. In addition, in the embodiment shown in FIG. 9, proximal end 912 and distal end 914 are rounded to reduce discomfort and irritation to surrounding tissue once inserted under the skin of the patient.

The insertable cardiac monitor 900 includes an accelerometer as well as electrodes. In particular, proximal electrode 904 and distal electrode 906 may be used to sense cardiac signals for determining abnormal cardiac events (e.g., bradycardia, tachycardia, etc.). ECG signals may be stored in a memory of the insertable cardiac monitor 900, and ECG data may be transmitted via integrated antenna 922 to another medical device, which may be another implantable device or an external device, or to a remote monitoring center. In alternative applications, electrodes 904 and 906 may be used for sensing any bio-potential signal of interest, which may be, for example, an EGM, EEG, EMG, or a nerve signal, from any implanted location.

In the embodiment shown in FIG. 9, proximal electrode 904 is in close proximity to the proximal end 912 and distal electrode 906 is in close proximity to distal end 914. In this embodiment, distal electrode 906 is not limited to a flattened, outward facing surface, but may extend from first major surface 908 around rounded edges 916 and onto the second major surface 910 so that the electrode 906 has a three-dimensional curved configuration. In the embodiment shown in FIG. 9, proximal electrode 904 is located on first major surface 908 and is substantially flat, outward facing. However, in other embodiments proximal electrode 904 may utilize the three dimensional curved configuration of distal electrode 906, providing a three dimensional proximal electrode (not shown in this embodiment). Similarly, in other embodiments distal electrode 906 may utilize a substantially flat, outward facing electrode located on first major surface 908 similar to that shown with respect to proximal electrode 904. The various electrode configurations allow for configurations in which proximal electrode 904 and distal electrode 906 are located on both first major surface 908 and second major surface 910. In other configurations, such as that shown in FIG. 9, only one of proximal electrode 904 and distal electrode 906 is located on both major surfaces 908 and 910, and in still other configurations both proximal electrode 904 and distal electrode 906 are located on one of the first major surface 908 or the second major surface 910 (i.e., proximal electrode 904 located on first major surface 908 while distal electrode 906 is located on second major surface 910). In another embodiment, insertable monitoring device 900 may include electrodes on both major surface 908 and 910 at or near the proximal and distal ends of the device, such that a total of four electrodes are included on insertable monitoring device 900. Electrodes 904 and 906 may be formed of a plurality of different types of biocompatible conductive material, e.g. stainless steel, titanium, platinum, iridium, or alloys thereof, and may utilize one or more coatings such as titanium nitride or fractal titanium nitride.

In the embodiment shown in FIG. 9, proximal end 912 includes a header assembly 920 that includes one or more of proximal electrode 904, integrated antenna 922, anti-migration projections 924, and/or suture hole 926. Integrated antenna 922 is located on the same major surface (i.e., first major surface 908) as proximal electrode 904 and is also included as part of header assembly 920. Integrated antenna 922 allows insertable monitoring device 900 to transmit and/or receive data. In other embodiments, integrated antenna 922 may be formed on the opposite major surface as proximal electrode 904, or may be incorporated within the housing 922 of insertable monitoring device 900. In one embodiment, electronic circuitry (not shown) may be housed within housing 922. As described above with respect to FIG. 1, electronic circuitry may include a tangible medium for storing baseline and threshold levels with respect to triggering events, as well as monitored, captured, and processed accelerometer signals and ECG signals/segments. In addition, electronic circuitry may include sensing circuitry for sensing one or more physiological parameters, such as ECG signals and accelerometer signals. Electronic circuitry may further include a processor module for processing accelerometer signals at a reduced sampling rate and at non-regular intervals and ECG signals to detect arrhythmic ECG segments.

In the embodiment shown in FIG. 9, anti-migration projections 924 are located adjacent to integrated antenna 922 and protrude away from first major surface 908 to prevent longitudinal movement of the device. In the embodiment shown in FIG. 9, anti-migration projections 924 includes a plurality (e.g., nine) small bumps or protrusions extending away from first major surface 908. As discussed above, in other embodiments anti-migration projections 924 may be located on the opposite major surface as proximal electrode 904 and/or integrated antenna 922. In addition, in the embodiment shown in FIG. 9 header assembly 920 includes suture hole 926, which provides another means of securing insertable monitoring device 900 to the patient to prevent movement following insert. In the embodiment shown, suture hole 926 is located adjacent to proximal electrode 904. In one embodiment, header assembly 920 is a molded header assembly made from a polymeric or plastic material, which may be integrated or separable from the main portion of insertable monitoring device 900.

Discussion of Possible Embodiments

The following are non-exclusive descriptions of possible embodiments of the present invention.

A method of monitoring a patient comprising generating an accelerometer signal of a patient via a patient medical device and sampling the accelerometer signal at a sampling rate that utilizes non-regular timing intervals.

The method of the preceding paragraph can optionally include, additionally and/or alternatively any, one or more of the following features, configurations and/or additional components.

The method may further include wherein the sampling rate is a second sampling rate and further comprising a first sampling rate, wherein the accelerometer signal is sampled at the first sampling rate before the accelerometer signal is sampled at the second sampling rate, wherein the first sampling rate is much higher than the second sampling rate.

The method may further include wherein the sampled accelerometer signal retains low frequency content and high frequency content.

The method may further include wherein the low frequency content includes posture information and the high frequency content includes activity information.

The method may further include wherein at least one of the posture information and activity information is utilized to prioritize a reporting of one or more arrhythmic episodes.

The method may further include wherein at least one of the posture information and activity information is utilized to determine a severity level of one or more arrhythmic episodes.

The method may further include wherein the severity level of the arrhythmia is high if a tachycardia is detected and the activity level of the patient is one or more of sedentary or low.

The method may further include wherein the severity level of the arrhythmia is high if a bradycardia is detected and the activity level of the patient is one or more of low or higher.

The method may further include wherein at least one of the posture information and activity information is utilized to determine a level of debilitation of a patient.

The method may further include wherein at least one of the posture information and activity information is communicated to a remote monitoring center.

The method may further include extracting patient activity and posture information from the captured and processed accelerometer signal.

The method may further include reporting an activity profile, the activity profile including the extracted patient activity and posture information.

In another embodiment, a patient medical device comprises sensors for monitoring an accelerometer signal of a patient; and circuitry for sampling the accelerometer signal at a sampling rate that utilizes non-regular timing intervals.

The method of the preceding paragraph can optionally include, additionally and/or alternatively any, one or more of the following features, configurations and/or additional components.

The medical device may further include wherein the sampling rate is a second sampling rate and further comprising a first sampling rate, wherein the accelerometer signal is sampled at the first sampling rate before the accelerometer signal is sampled at the second sampling rate, wherein the first sampling rate is much higher than the second sampling rate.

The medical device may further include wherein the sampled accelerometer signal retains low frequency content and high frequency content, the low frequency content including posture information and the high frequency content include activity information.

The medical device may further include wherein at least one of the posture information and activity information is utilized to construct an activity profile.

The medical device may further include wherein at least one of the posture information and activity information is utilized to prioritize a reporting of one or more arrhythmic episodes.

The medical device may further include wherein at least one of the posture information and activity information is utilized to determine a severity level of one or more arrhythmic episodes.

The medical device may further include wherein at least one of the posture information and activity information is utilized to determine a level of debilitation of a patient.

The medical device may further include sensors for monitoring an electrocardiogram (ECG) signal of a patient.

Another embodiment provides a method of processing physiological signals comprising monitoring ECG signals and accelerometer signals of a patient via a patient medical device and capturing an ECG segment and sampling the accelerometer signal at a sampling rate that utilizes non-regular timing intervals.

The method of the preceding paragraph can optionally include, additionally and/or alternatively any, one or more of the following features, configurations and/or additional components.

The method may further include wherein the sampling rate is a second sampling rate and further comprising a first sampling rate, wherein the accelerometer signal is sampled at the first sampling rate before the accelerometer signal is sampled at the second sampling rate, wherein the first sampling rate is much higher than the second sampling rate.

The method may further include wherein all monitored ECG signals are captured and stored and all accelerometer signals are sampled and stored.

The method may further include wherein the stored ECG signals and accelerometer signals are communicated to a remote monitoring center.

The method may further include wherein the accelerometer signal is sampled in response to a triggering event based on the ECG segment.

The method may further include wherein the triggering event is an abnormal ECG segment.

The method may further include wherein the ECG segment is captured in response to a triggering event based on the accelerometer signal.

The method may further include wherein the triggering event is an abnormal accelerometer signal.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A method of monitoring a patient, comprising:
generating an accelerometer signal of a patient via a patient medical device;
sampling the accelerometer signal, without using an anti-aliasing low-pass filter, at a reduced sampling rate that utilizes non-regular timing intervals, wherein the sampling at non-regular timing intervals includes sampling according to the formula: $(t_n+\Delta)$, wherein $t_n$ is a sampling time at a regular interval n and $\Delta$ is a random or pseudo random integer independently selected for each $t_n$,
wherein the sampled accelerometer signal retains low frequency content including posture information and high frequency content including activity information, and
wherein at least one of the posture information and activity information is utilized to determine a severity level of one or more arrhythmic episodes.

2. The method of claim 1, wherein at least one of the posture information and activity information is utilized to prioritize a reporting of one or more arrhythmic episodes.

3. The method of claim 1, wherein the severity level of the arrhythmia is high if a tachycardia is detected and the activity level of the patient is characterized as sedentary or at rest.

4. The method of claim 1, wherein the severity level of the arrhythmia is high if a bradycardia is detected and the activity level of the patient is characterized as active.

5. The method of claim 1, wherein at least one of the posture information and activity information is utilized to determine a level of debilitation of a patient.

6. The method of claim 1, wherein at least one of the posture information and activity information is communicated to a remote monitoring center.

7. The method of claim 1, further comprising extracting patient activity and posture information from the captured and processed accelerometer signal.

8. The method of claim 1, further comprising reporting an activity profile, the activity profile including the extracted patient activity and posture information.

9. The method of claim 1, wherein the reduced sampling rate is about 10 Hz or less.

10. A patient medical device, comprising: sensors for monitoring an accelerometer signal of a patient; and circuitry for sampling the accelerometer signal, without using an anti-aliasing low-pass filter, at a reduced sampling rate that utilizes non-regular timing intervals, wherein the sampling at non-regular timing intervals includes sampling according to the formula: $(t_n+\Delta)$, wherein $t_n$ is a sampling time at a regular interval n and $\Delta$ is a random or pseudo random integer independently selected for each $t_n$,
wherein the sampled accelerometer signal retains low frequency content and high frequency content, the low frequency content including posture information and the high frequency content include activity information, and
wherein at least one of the posture information and activity information is utilized to determine a severity level of one or more arrhythmic episodes.

11. The patient medical device of claim 10, wherein at least one of the posture information and activity information is utilized to construct an activity profile.

12. The patient medical device of claim 10, wherein at least one of the posture information and activity information is utilized to prioritize a reporting of one or more arrhythmic episodes.

13. The patient medical device of claim 10, wherein at least one of the posture information and activity information is utilized to determine a level of debilitation of a patient.

14. The patient medical device of claim 10, further comprising sensors for monitoring an electrocardiogram (ECG) signal of a patient.

15. The method of claim 10, wherein the reduced sampling rate is about 10 Hz or less.

16. A method of processing physiological signals, comprising:
monitoring ECG signals and accelerometer signals of a patient via a patient medical device; and
capturing an ECG segment and sampling the accelerometer signal, wherein the accelerometer signal is sampled, without using an anti-aliasing low-pass filter, at a reduced sampling rate that utilizes non-regular timing intervals, wherein the sampling at non-regular timing intervals includes sampling according to the formula: $(t_n+\Delta)$, wherein $t_n$ is a sampling time at a regular interval n and $\Delta$ is a random or pseudo random integer independently selected for each $t_n$,
wherein the accelerometer signal is sampled in response to a triggering event based on the ECG segment.

17. The method of claim 16, wherein all monitored ECG signals are captured and stored and all accelerometer signals are sampled and stored.

18. The method of claim 17, wherein the stored ECG signals and accelerometer signals are communicated to a remote monitoring center.

19. The method of claim 16, wherein the triggering event is an abnormal ECG segment.

20. The method of claim 16, wherein the ECG segment is captured in response to a triggering event based on the accelerometer signal.

21. The method of claim 20, wherein the triggering event is an abnormal accelerometer signal.

22. The method of claim 16, wherein the reduced sampling rate is about 10 Hz or less.

* * * * *